(12) United States Patent
Fernando et al.

(10) Patent No.: US 10,376,212 B2
(45) Date of Patent: Aug. 13, 2019

(54) MUSCLE FATIGUE OUTPUT DEVICE, MUSCLE FATIGUE OUTPUT METHOD, AND RECORDING MEDIUM

(71) Applicant: Panasonic Intellectual Property Management Co., Ltd., Osaka (JP)

(72) Inventors: Jeffry Fernando, Osaka (JP); Jun Ozawa, Nara (JP); Mototaka Yoshioka, Osaka (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 211 days.

(21) Appl. No.: 15/607,970

(22) Filed: May 30, 2017

(65) Prior Publication Data

US 2017/0354377 A1    Dec. 14, 2017

(30) Foreign Application Priority Data

Jun. 10, 2016    (JP) .................................. 2016-116666

(51) Int. Cl.
| | | |
|---|---|---|
| *A61N 1/00* | (2006.01) | |
| *A61B 5/00* | (2006.01) | |
| *A61B 5/0488* | (2006.01) | |
| *G16H 50/70* | (2018.01) | |
| *A61B 5/04* | (2006.01) | |

(52) U.S. Cl.
CPC .......... *A61B 5/6843* (2013.01); *A61B 5/0488* (2013.01); *A61B 5/4519* (2013.01); *G16H 50/70* (2018.01); *A61B 5/04* (2013.01)

(58) Field of Classification Search
CPC ... A61B 5/6843; A61B 5/0488; A61B 5/4519; A61B 5/04; G16H 50/78; G06H 19/00
See application file for complete search history.

(56) References Cited

FOREIGN PATENT DOCUMENTS

JP    2015-062658    4/2015

OTHER PUBLICATIONS

Tohru Kiryu et al., "Providing Appropriate Exercise Levels for the Elderly", IEEE Engineering in Medicine and Biology Magazine, vol. 20, No. 6, pp. 116-124, Nov.-Dec. 2001.

*Primary Examiner* — Lindsey G Wehrheim
(74) *Attorney, Agent, or Firm* — Wenderoth, Lind & Ponack, L.L.P.

(57) ABSTRACT

A muscle fatigue output device is provided with a myoelectric measurement unit that acquires myoelectricity of a user, and a main control unit that determines fatigue of a muscle of the user on the basis of the myoelectricity. The main control unit (a) uses the myoelectricity to acquire a value for a frequency characteristic of the myoelectricity, (b) uses the myoelectricity to acquire a value for an amplitude characteristic of the myoelectricity, (c) acquires a ratio between the value for the frequency characteristic and the value for the amplitude characteristic as an index for the fatigue of the muscle of the user, and (d) outputs information regarding the fatigue of the muscle of the user, on the basis of the index for the fatigue of the muscle of the user.

11 Claims, 43 Drawing Sheets

EMG WAVEFORM

CASE A3: SUBJECT 2, BICEPS, 5 kg

CASE A4: SUBJECT 3, BICEPS, 5 kg

CASE B2: SUBJECT 1, TRICEPS, 7.5 kg (FIRST TIME)

CASE A1: SUBJECT 1, BICEPS, 5 kg (FIRST TIME)

CASE B1: SUBJECT 1, BICEPS, 7.5 kg (FIRST TIME)

CASE A3: SUBJECT 2, BICEPS, 5 kg

CASE A4: SUBJECT 3, BICEPS, 5 kg

CASE B2: SUBJECT 1, TRICEPS, 7.5 kg (FIRST TIME)

CASE B4: SUBJECT 1, TRICEPS, 7.5 kg (SECOND TIME)

FIG. 43

| | INITIAL VALUE | BASELINE |
|---|---|---|
| CASE A1: SUBJECT 1, BICEPS, 5 kg (FIRST TIME) | 0.2991 | 0.2503 |
| CASE A2: SUBJECT 1, BICEPS, 5 kg (SECOND TIME) | 0.4351 | 0.2485 |
| CASE B1: SUBJECT 1, BICEPS, 7.5 kg (FIRST TIME) | 0.2950 | 0.2504 |
| CASE B3: SUBJECT 1, BICEPS, 7.5 kg (SECOND TIME) | 0.3222 | 0.2500 |
| CASE A3: SUBJECT 2, BICEPS, 5 kg | 0.7602 | 0.2441 |
| CASE A4: SUBJECT 3, BICEPS, 5 kg | 1.0090 | 0.2409 |
| CASE B2: SUBJECT 1, TRICEPS, 7.5 kg (FIRST TIME) | 3.6689 | 0.2112 |
| CASE B4: SUBJECT 1, TRICEPS, 7.5 kg (SECOND TIME) | 4.5947 | 0.2025 |

FIG. 44

| | SLOPE | INTERCEPT | BASELINE |
|---|---|---|---|
| CASE A1: SUBJECT 1, BICEPS, 5 kg (FIRST TIME) | -0.0011 | 0.3283 | 0.2512 |
| CASE A2: SUBJECT 1, BICEPS, 5 kg (SECOND TIME) | -0.0007 | 0.4439 | 0.2503 |
| CASE B1: SUBJECT 1, BICEPS, 7.5 kg (FIRST TIME) | -0.0020 | 0.3199 | 0.2507 |
| CASE B3: SUBJECT 1, BICEPS, 7.5 kg (SECOND TIME) | -0.0007 | 0.3268 | 0.2515 |
| CASE A3: SUBJECT 2, BICEPS, 5 kg | -0.0042 | 0.8082 | 0.2444 |
| CASE A4: SUBJECT 3, BICEPS, 5 kg | -0.0043 | 0.9316 | 0.2432 |
| CASE B2: SUBJECT 1, TRICEPS, 7.5 kg (FIRST TIME) | -0.0314 | 4.0721 | 0.2037 |
| CASE B4: SUBJECT 1, TRICEPS, 7.5 kg (SECOND TIME) | -0.0163 | 4.9180 | 0.2048 |

MUSCLE FATIGUE OUTPUT DEVICE, MUSCLE FATIGUE OUTPUT METHOD, AND RECORDING MEDIUM

BACKGROUND

1. Technical Field

The present disclosure relates to a muscle fatigue output device, a muscle fatigue output method, and a recording medium that output information regarding muscle fatigue from myoelectricity. More specifically, the present disclosure relates to a muscle fatigue output device and the like that output information regarding muscle fatigue using a frequency characteristic and an amplitude characteristic of myoelectricity such as myoelectric potentials.

2. Description of the Related Art

An electromyogram is a diagram obtained by individual action potentials generated from muscle fibers being added when the action potentials have reached electrodes by means of volume conduction. An electromyogram expresses the extent to which and the way in which a muscular action potentials are generated when a muscle contracts and muscular strength is exhibited, in other words, expresses the degree of involvement of a motor unit.

In T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001, a method is disclosed for evaluating muscle fatigue from myoelectric potentials serving as myoelectricity. A myoelectric potential waveform that periodically changes is produced by a muscle repeatedly contracting and extending, as depicted in FIG. 1, for example. It should be noted that FIG. 1 is a drawing depicting an example of a myoelectric potential waveform that periodically appears, namely an EMG waveform, in which the vertical axis indicates the myoelectric potential (unit: μV) and the horizontal axis indicates time (unit: seconds). The carrying out of one contraction and one extension of a muscle is considered to be one muscle exercise cycle. In the EMG waveform, antinodes indicate a contraction of the muscle, and nodes indicate an extension of the muscle. In a method for evaluating muscle fatigue, five cycles of EMG waveforms, namely myoelectric potentials, serve as one frame, and an average rectified value (ARV) and a mean frequency (MNF) are obtained in each frame. In addition, 24 frames are set as one block, and a correlation coefficient of the ARV and MNF is obtained for each block while shifting one frame at a time. Changes in the correlation coefficient serve as an index for muscle fatigue. When a muscle fatigues, there is a tendency for the ARV to increase and the MNF to decrease, and therefore the correlation coefficient has a tendency to decrease gradually.

Japanese Unexamined Patent Application Publication No. 2015-62658 discloses a method for evaluating muscle fatigue from myoelectric potentials. In this method, a frequency band for myoelectric potentials is divided into three frequency bands: a slow muscle band (20 to 45 Hz), an intermediate muscle band (45 to 81 Hz), and a fast muscle band (81 to 350 Hz). For example, FIG. 17 depicts an example of the aforementioned three frequency bands given in Japanese Unexamined Patent Application Publication No. 2015-62658. In FIG. 17, the vertical axis indicates the power spectrum of myoelectric potential signals and the horizontal axis indicates frequency (unit: Hz). In Japanese Unexamined Patent Application Publication No. 2015-62658, the sum of power values in each frequency band is calculated. In addition, the proportion ($r_L$) of the sum of the power values in the slow muscle band with respect to the total power in the three frequency bands, the proportion ($r_M$) of the sum of the power values in the intermediate muscle band with respect to said total power, and the proportion ($r_H$) of the sum of the power values in the fast muscle band with respect to said total power are calculated at each fixed time. Changes in $r_L$, $r_M$, and $r_H$ with respect to time are exhibited, as depicted in FIG. 18, for example. Also, when $r_L > r_H$, it is determined that a muscle fatigue state is in effect. In addition, when the muscle fatigue state is determined as being in effect, a warning is issued to the user. It should be noted that in FIG. 18, the horizontal axis indicates the elapsed time (unit: seconds) and the vertical axis indicates the use proportion of muscle fibers (unit: %).

In T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001 and Japanese Unexamined Patent Application Publication No. 2015-62658, there is a problem in that when muscle fatigue is evaluated from myoelectric potentials, there are cases where the muscle fatigue state has not actually been reached even though it is determined that the muscle fatigue state is in effect, and where the muscle fatigue state has actually been reached even though it is determined that the muscle fatigue state has not been reached. Specifically, for example, when muscle fatigue of the upper arm muscles is evaluated, muscle fatigue of the biceps and muscle fatigue of the triceps are evaluated with there being some confusion therebetween.

SUMMARY

One non-limiting exemplary aspect of the present disclosure provides a muscle fatigue output device, a muscle fatigue output method, and a recording medium with which the accuracy of output information regarding muscle fatigue is improved using a frequency characteristic and an amplitude characteristic of myoelectricity.

In one general aspect, the techniques disclosed here feature a muscle fatigue output device provided with: a myoelectric sensor that acquires myoelectricity of a user; and a control unit, the control unit (a) using the myoelectricity to acquire a value for a frequency characteristic of the myoelectricity, (b) using the myoelectricity to acquire a value for an amplitude characteristic of the myoelectricity, (c) acquiring a ratio between the value for the frequency characteristic and the value for the amplitude characteristic as an index for fatigue of a muscle of the user, and (d) outputting information that is based on the index for the fatigue of the muscle of the user.

General or specific aspects of the aforementioned may be realized using a device, a system, a method, an integrated circuit, a computer program, or a recording medium such as a computer-readable recording disk, and may be realized using an arbitrary combination of a device, a system, a method, an integrated circuit, a computer program, and a recording medium. A computer-readable recording medium includes a nonvolatile recording medium such as a compact disc read-only memory (CD-ROM).

According to the present disclosure, it is possible to improve the accuracy of output information by using a frequency characteristic and an amplitude characteristic of myoelectricity. Additional benefits and advantages of the aspects of the present disclosure will become apparent from the present specification and drawings. The benefits and/or advantages may be individually provided by the various aspects and features disclosed in the present specification and drawings, and need not all be necessary in order to obtain one or more of the same.

BRIEF DESCRIPTION OF THE DRAWINGS

FIG. 43 is a drawing depicting an example of a method for determining a baseline in processing performed by the muscle fatigue output device according to embodiment 1; and FIG. 44 is a drawing depicting another example of a method for determining a baseline in processing performed by the muscle fatigue output device according to embodiment 1.

DETAILED DESCRIPTION (Findings Forming the Basis for the Present Disclosure)

Figure 1:
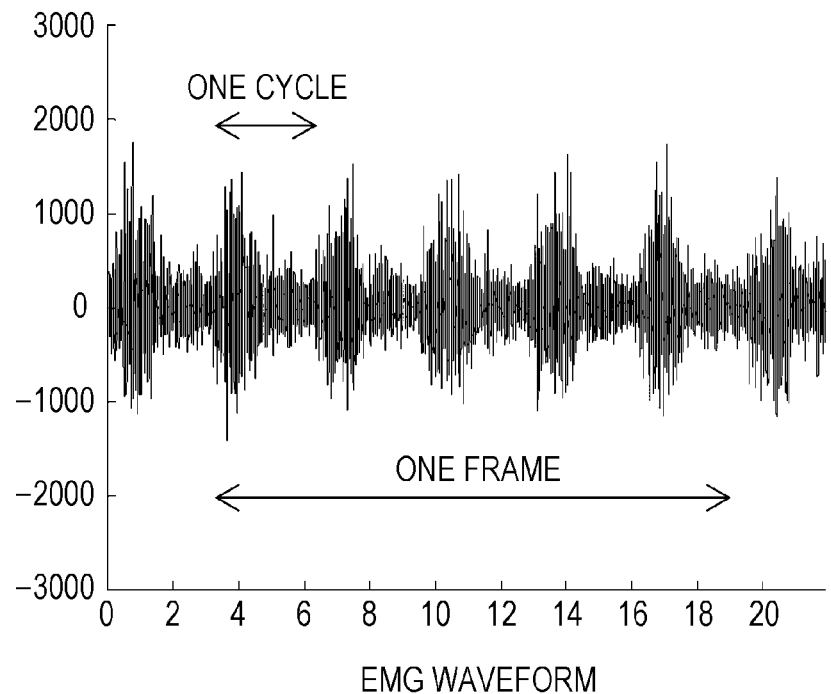
FIG. 1 is a drawing depicting an example of an EMG waveform that appears periodically.
Figure 2:
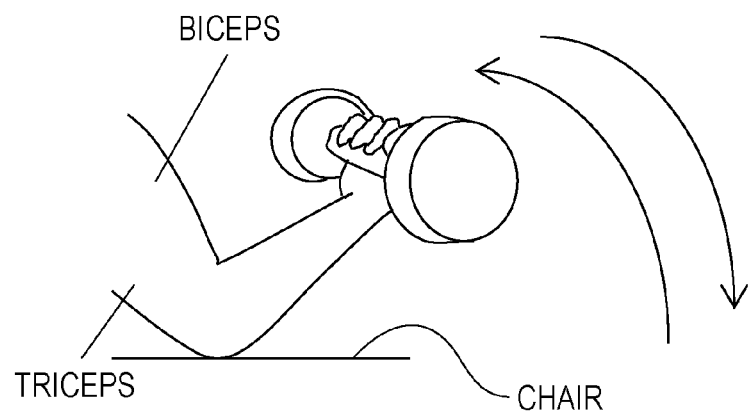
FIG. 2 is a drawing depicting an overview of an example of an experiment for evaluating muscle fatigue from myoelectric potentials.

The inventors involved in the present disclosure carried out an experiment for evaluating muscle fatigue from myoelectric potentials, and using the methods described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001 and Japanese Unexamined Patent Application Publication No. 2015-62658, carried out muscle fatigue evaluations. FIG. 2 is a drawing depicting an overview of an example of an experiment for evaluating muscle fatigue from myoelectric potentials. In this experiment, a subject fixes his or her elbow on a chair, and holds a dumbbell in a hand. Then, the subject repeats a dumbbell curl, which is a bending and stretching exercise of the elbow, that is, an exercise performed by contracting and extending the biceps, until fatigue of the biceps reaches the limit thereof. Specifically, two kinds of experiments A and B given hereinafter were carried out.

[Experiment A]

The subject holds a 5-kg dumbbell in a hand and performs the bending and stretching exercise of the elbow. In this experiment, the myoelectric potentials of the biceps are measured.

[Experiment B]

The subject holds a 7.5-kg dumbbell in a hand and performs the bending and stretching exercise of the elbow. In this experiment, the myoelectric potentials of the biceps and the triceps are measured at the same time. In this case, the elbow is fixed to a chair, and therefore fatigue occurs in the biceps but does not occur in the triceps.

Figure 3:
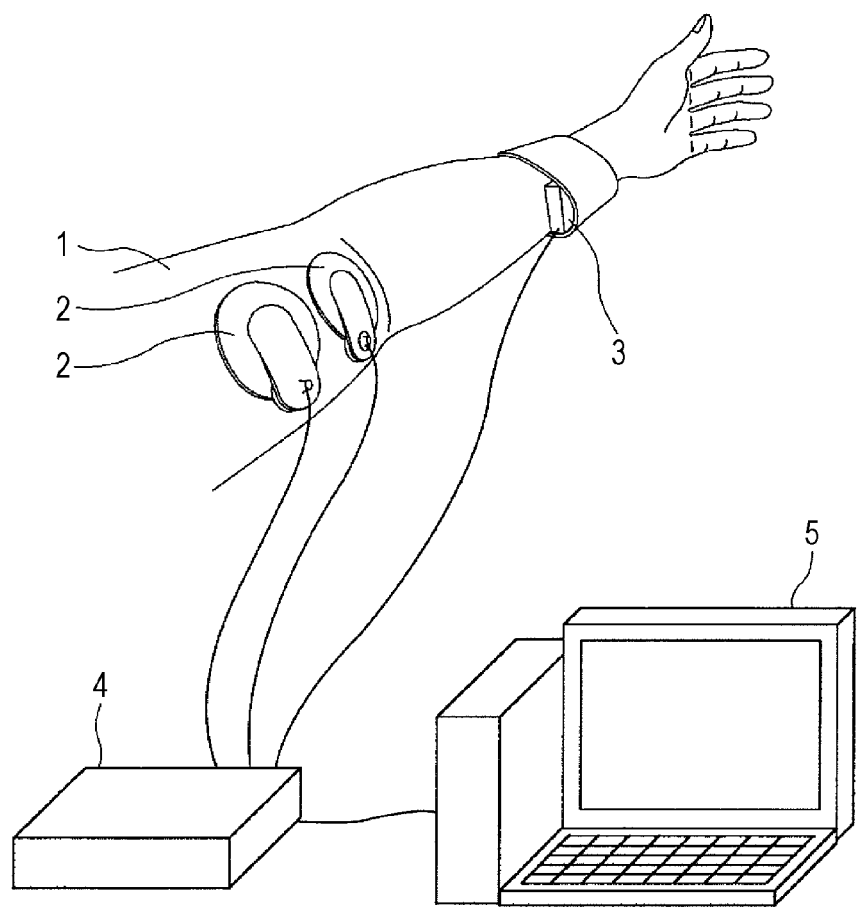
FIG. 3 is a drawing depicting the arrangement of electrodes and the like for measuring myoelectric potentials in the experiment of FIG. 2.

FIG. 3 is a drawing depicting the arrangement of electrodes 2 and the like for measuring myoelectric potentials in the experiment of FIG. 2, specifically experiment A. In FIG. 3, on an arm 1 of the subject, two electrodes 2 are arranged in order to detect action potentials of the biceps. In addition, in FIG. 3, an acceleration sensor 3 is attached to the wrist in order to accurately obtain repeated cycles of the bending and stretching exercise of the elbow. The acceleration sensor 3 may be any of a uniaxial acceleration sensor, a biaxial acceleration sensor, and a triaxial acceleration sensor. The electrodes 2 and the acceleration sensor 3 are electrically connected to a signal processor 4 that includes an A/D converter or the like, and the signal processor 4 is electrically connected to an arithmetic unit 5 such as a computer. The signal processor 4 may carry out processing such as eliminating noise from analog signals received from the electrodes 2 and the acceleration sensor 3, amplifying analog signals, and converting analog signals into digital signals. The arithmetic unit 5 may process signals received from the signal processor 4, and output measurement results of the electrodes 2 and the acceleration sensor 3 using an electromyogram, for example.

Figure 4:
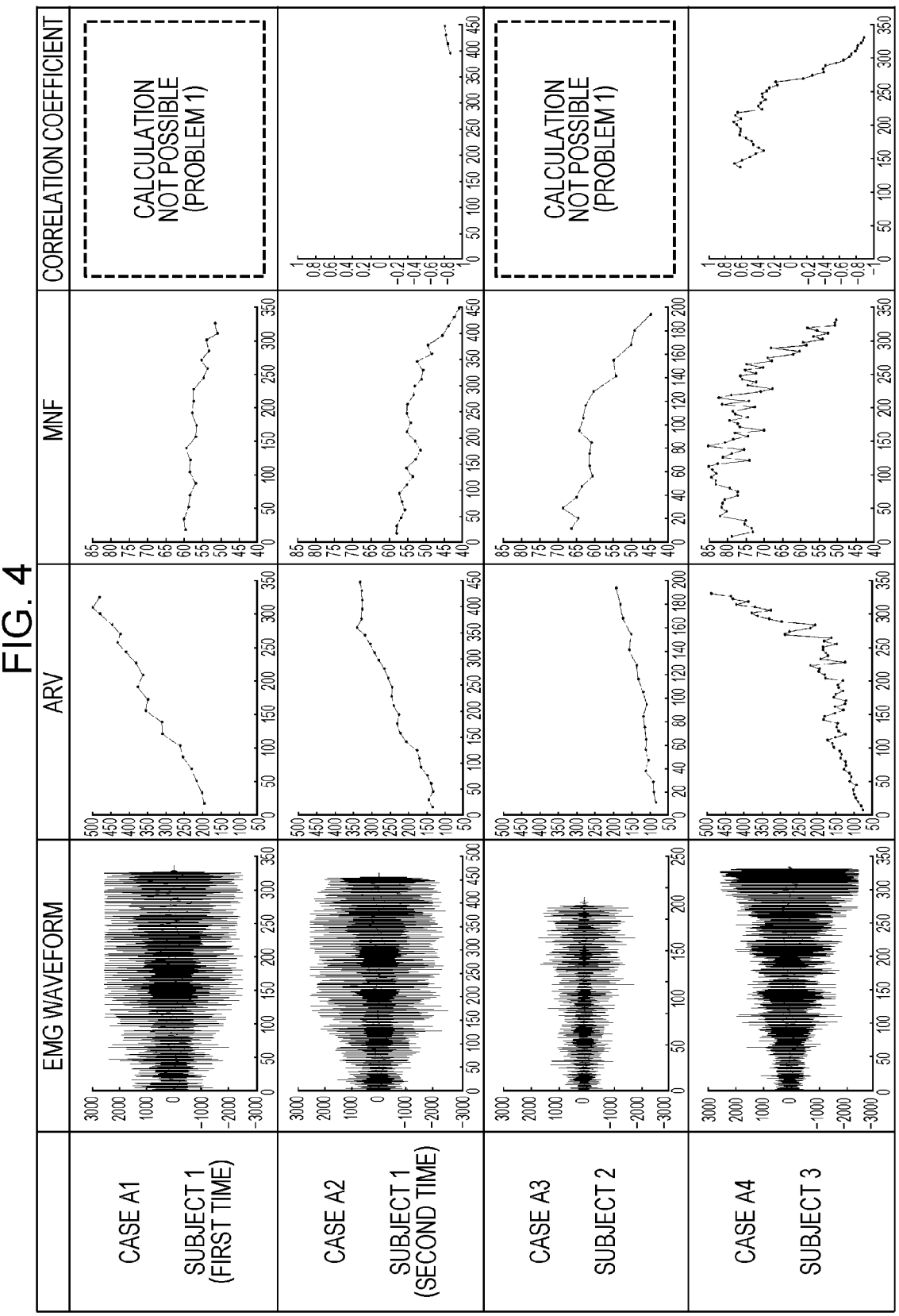
FIG. 4 is a drawing depicting experiment results with regards to each parameter when evaluating muscle fatigue in experiment A such as that depicted in FIG. 2, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001.

FIG. 4 depicts results with regards to each parameter of experiment A when evaluating muscle fatigue, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001. In experiment A, three subjects carried out the experiment, and experiment results for four cases were acquired. Subject 1 carried out the experiment twice, and subjects 2 and 3 each carried out the experiment once. FIG. 4 depicts experiment results for case A1 which are the first experiment results for subject 1, experiment results for case A2 which are the second experiment results for subject 1, experiment results for case A3 which are the first experiment results for subject 2, and experiment results for case A4 which are the first experiment results for subject 3. It should be noted that in the bending and stretching exercise of the elbow in cases A1 and A2, the bending angle of the elbow of subject 1 is the same, and therefore the load is the same. The parameters indicated in the experiment results for cases A1 to A4 are an EMG waveform, changes in the ARV calculated from the EMG waveform, changes in the MNF calculated from the EMG waveform, and a correlation coefficient calculated from the ARV and MNF. In each of the graphs for the EMG waveform, the changes in the ARV, the changes in the MNF, and the correlation coefficient depicted in FIG. 4, the horizontal axis indicates the elapsed time and the vertical axis indicates the myoelectric potential, the ARV value, the MNF value, and the correlation coefficient value.

Here, the correlation coefficient will be described. In the calculation of a correlation coefficient of the ARV and MNF, first, two or more ARVs and two or more MNFs are subtracted by the average values therefor. Thereafter, the covariance of ARV and MNF is calculated using the subtraction results, and the calculated covariance is divided by the standard deviation of the ARV and the standard deviation of the MNF. Thus, the correlation coefficient value is normalized within the range of −1 to 1. In order to calculate an accurate correlation coefficient of the ARV and MNF, it is necessary to increase the number of pieces of data for the ARV and MNF. For example, when using two ARVs and two MNFs, the correlation coefficient is able to take only the two values of −1 and 1.

Figure 6:
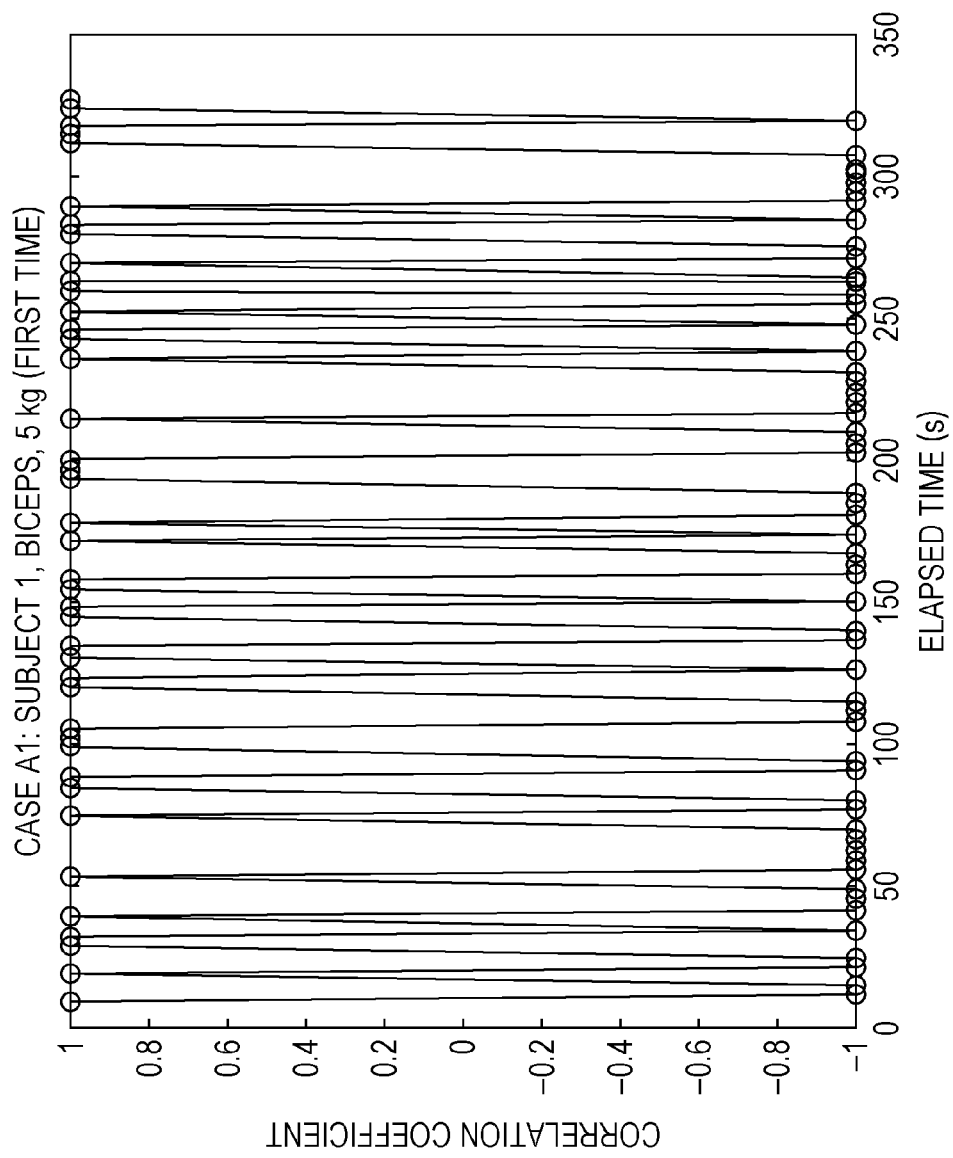
FIG. 6 is a drawing depicting an example of a correlation coefficient obtained when the calculation method is changed, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001.

FIG. 6 depicts an example in which, for example, in case A1, the myoelectric potentials of one cycle serve as one frame, and a correlation coefficient is calculated every two frames using data from the two frames. It should be noted that in FIG. 6, the horizontal axis indicates the elapsed time (unit: seconds) and the vertical axis indicates the correlation coefficient value. According to FIG. 6, the correlation coefficient value fluctuates between the values of either −1 or 1 as time elapses. Thus, if there is a small number of pieces of data in a time interval for calculating the correlation coefficient, the transition in the correlation coefficient is likely to fluctuate significantly.

Figure 7:
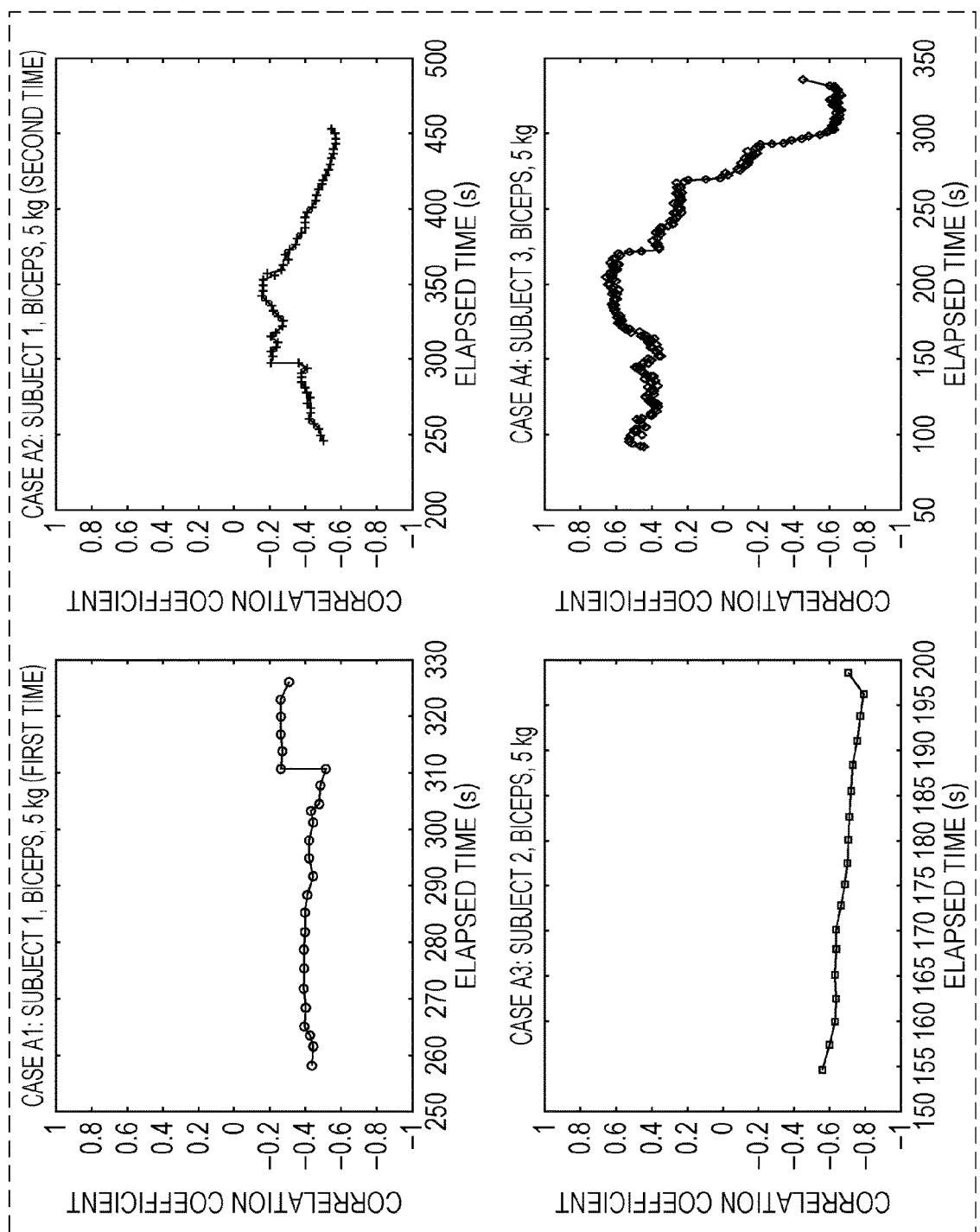
FIG. 7 is a drawing depicting other examples of correlation coefficients obtained when the calculation method is changed, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001.

Furthermore, data from 75 frames is necessary for fluctuation in the positive direction and negative direction of the correlation coefficient value to be attenuated in cases A1, A2, A3, and A4. FIG. 7 depicts examples in which the myoelectric potentials of one cycle serve as one frame, and correlation coefficients are calculated using data from 75 frames. It should be noted that in FIG. 7, the horizontal axes indicate the elapsed time (unit: seconds) and the vertical axes indicate the correlation coefficient value. In FIG. 7, the 75 frames correspond to the elapsed time from 92 to 258 seconds.

In the results for experiment A depicted in FIG. 4, in all of the cases A1 to A4, the ARV increases and the MNF decreases as time elapses.

Furthermore, the correlation coefficient obtained from the experiment results for subject 3 in case A4 decreases from a plus value to a minus value as time elapses. In the second experiment results for subject 1 in case A2, the correlation coefficient is already a minus value when obtained. Moreover, the correlation coefficient decreases as the muscle fatigues, and takes a minus value in the muscle fatigue state.

However, in the first experiment results for subject 1 in case A1 and the experiment results for subject 2 in case A3, there occurred a problem in that, at the point in time when the fatigue of the biceps had already reached the limit thereof, fatigue evaluation processing had not started, that is, the correlation coefficient had not been obtained. Hereinafter, this problem is referred to as problem 1. This is because the myoelectric potentials of 120 cycles (5 cycles per frame for 24 frames×5 cycles) are necessary to calculate the correlation coefficient. In short, data of a certain amount of time is necessary to calculate the correlation coefficient.

Figure 5:
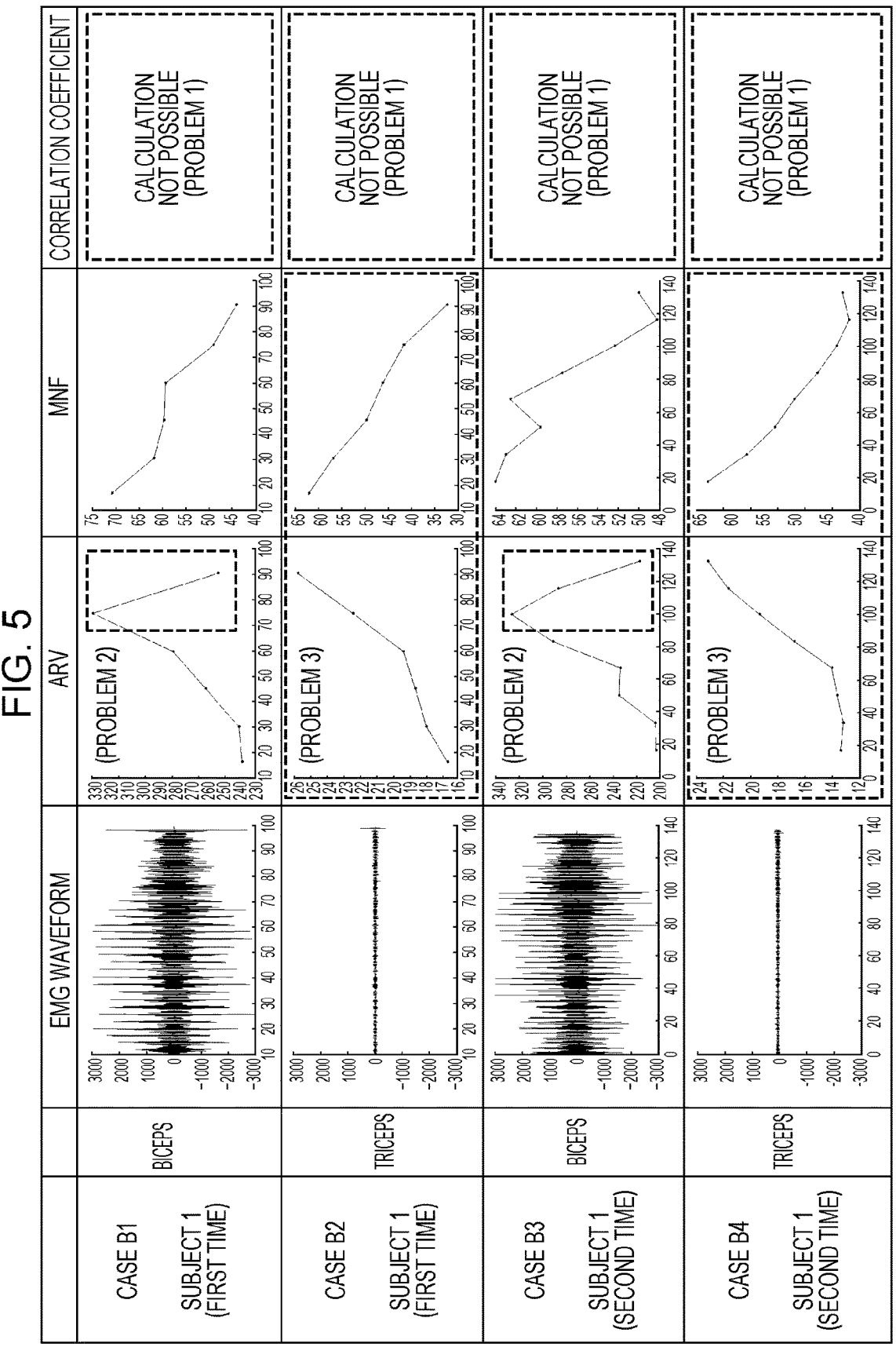
FIG. 5 is a drawing depicting experiment results with regards to each parameter when evaluating muscle fatigue in experiment B such as that depicted in FIG. 2, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001.

FIG. 5 depicts results with regards to each parameter of experiment B when evaluating muscle fatigue, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001. In experiment B, one subject carried out the experiment twice, and experiment results for four cases were acquired. FIG. 5 depicts first experiment results for subject 1 and second experiment results for subject 1. Specifically, FIG. 5 depicts experiment results for case B1 which are experiment results for the biceps of subject 1 in the first experiment, experiment results for case B2 which are experiment results for the triceps of subject 1 in the first experiment, experiment results for case B3 which are experiment results for the biceps of subject 1 in the second experiment, and experiment results for case B4 which are experiment results for the triceps of subject 1 in the second experiment. It should be noted that in the bending and stretching exercise of the elbow in cases B1 and B2 and the bending and stretching exercise of the elbow in cases B3 and B4, the bending angle of the elbow of subject 1 is the same, and therefore the load is the same. The parameters indicated in the experiment results for cases B1 to B4 are the EMG waveform, the changes in the ARV, the changes in the MNF, and the correlation coefficient, as in experiment A. In each of the graphs for the EMG waveform, the changes in the ARV, the changes in the MNF, and the correlation coefficient depicted in FIG. 5, the horizontal axis indicates the elapsed time and the vertical axis indicates the myoelectric potential, the ARV value, the MNF value, and the correlation coefficient value.

Problem 1 occurs in all of the cases B1 to B4, similar to the results for experiment A. In addition, in cases B1 and B3, the EMG waveform of the biceps decreases immediately before the muscle fatigue reaches the limit thereof; however, the ARV therefore decreases. Therefore, when muscle fatigue is evaluated using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001, a problem occurs in that an erroneous evaluation is reached. Hereinafter, this problem is referred to as problem 2. In addition, in cases B2 and B4, a phenomenon is seen in that the ARV increases and the MNF decreases even though the triceps is not fatigued. When muscle fatigue is evaluated using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001, a problem occurs in that said phenomenon is also evaluated as muscle fatigue having occurred. Hereinafter, this problem is referred to as problem 3.

Figure 8:
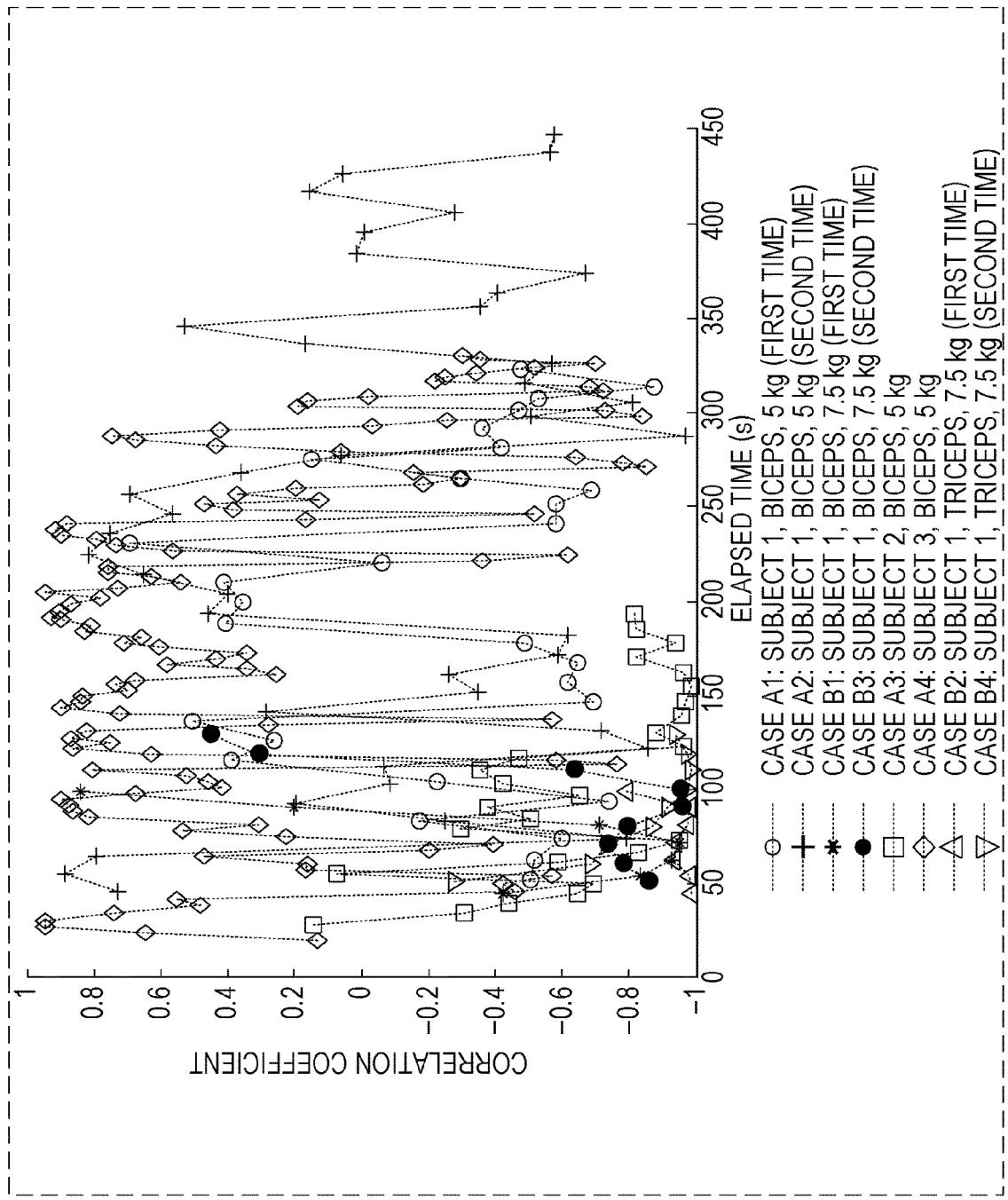
FIG. 8 is a drawing depicting results for experiment A and experiment B when the number of pieces of data necessary to calculate a correlation coefficient is reduced, using the method described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001.
Figure 9:
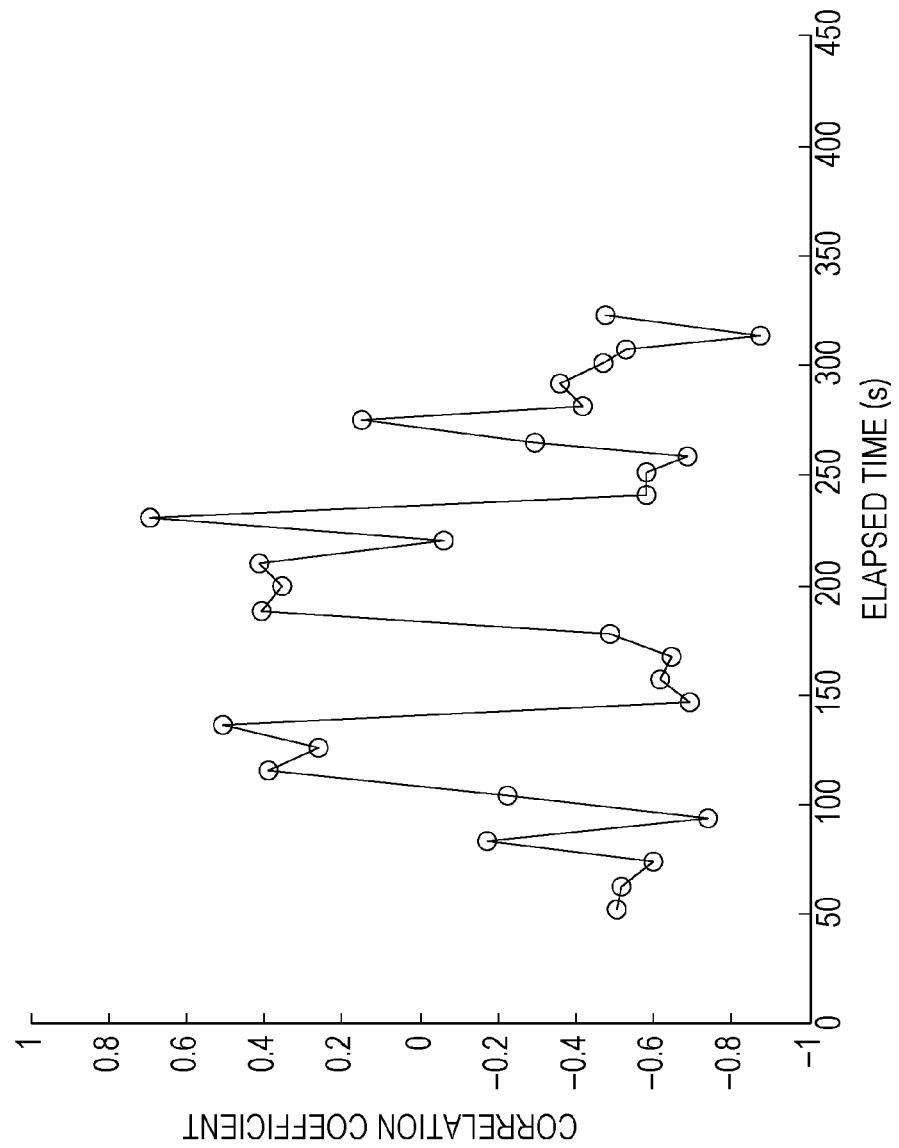
FIG. 9 is a drawing separately depicting experiment results for case A1, which is one of the plurality of cases in FIG. 8.
Figure 10:
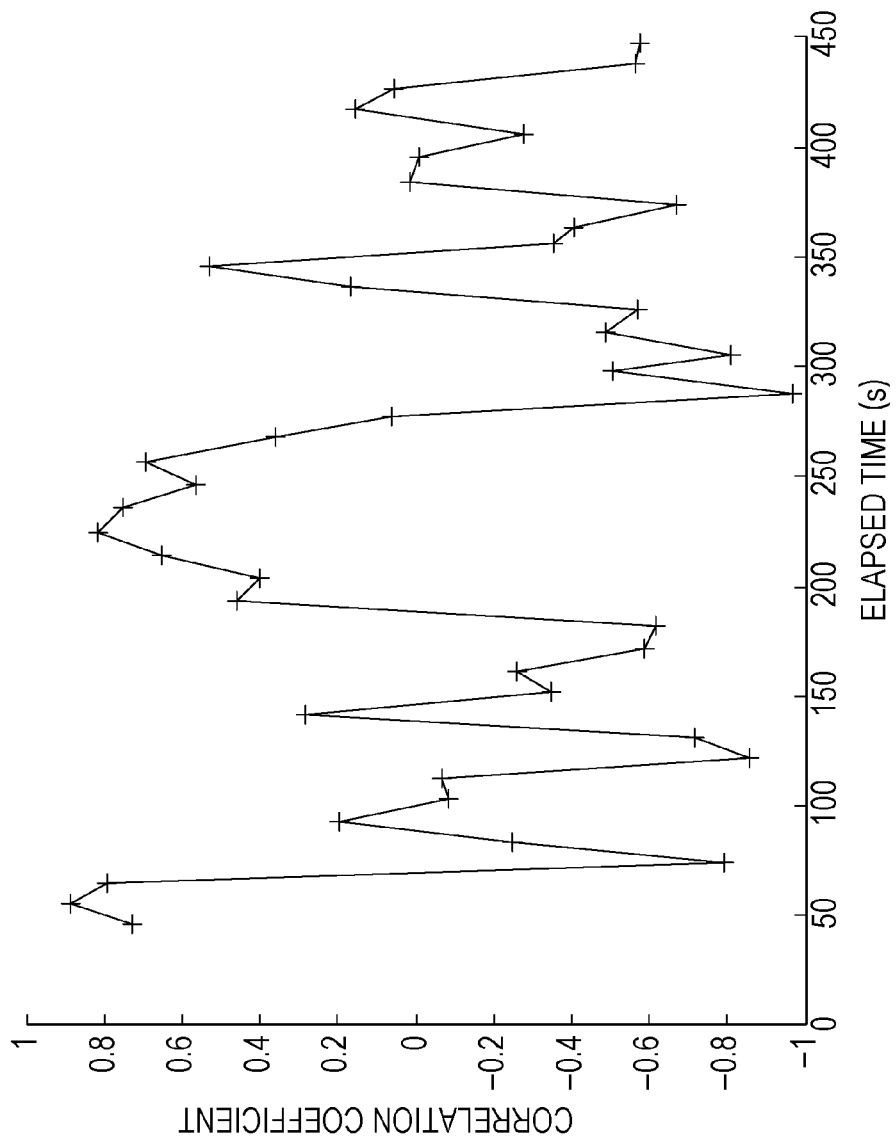
FIG. 10 is a drawing separately depicting experiment results for case A2, which is one of the plurality of cases in FIG. 8.
Figure 11:
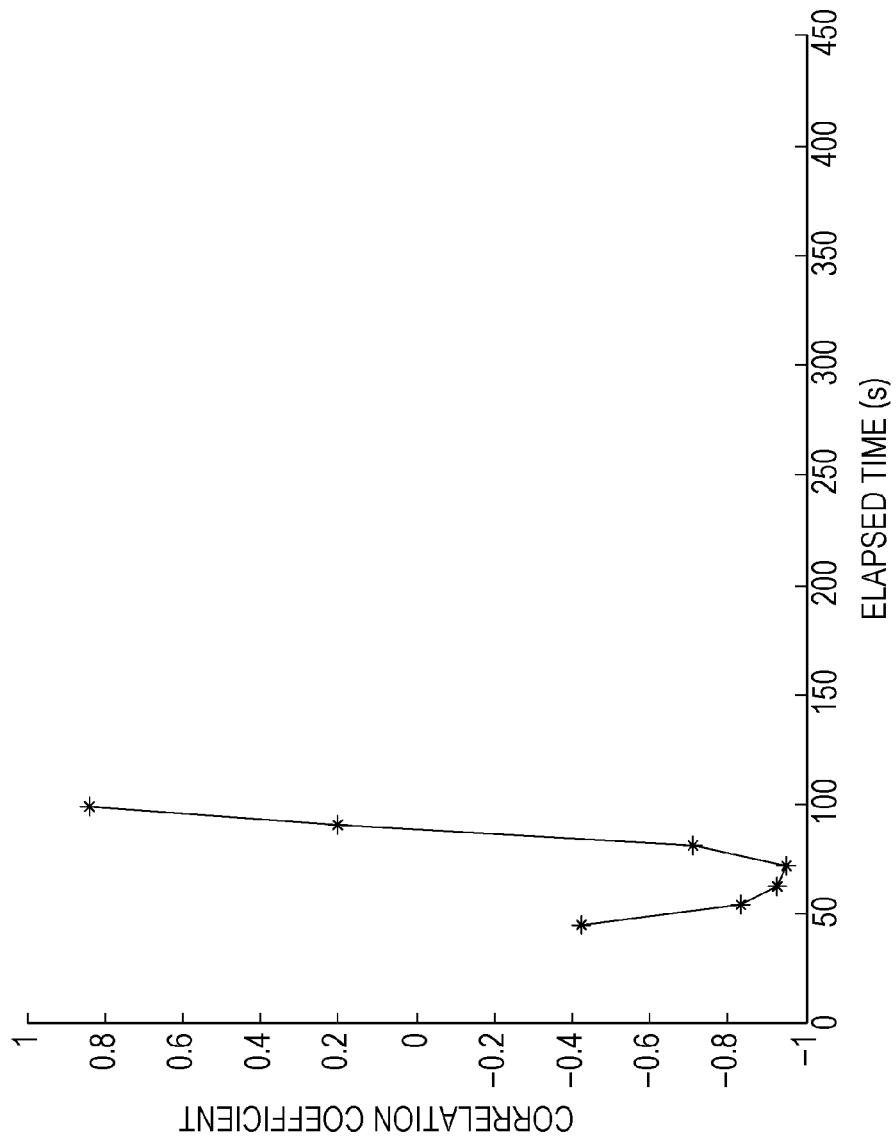
FIG. 11 is a drawing separately depicting experiment results for case B1, which is one of the plurality of cases in FIG. 8.
Figure 12:
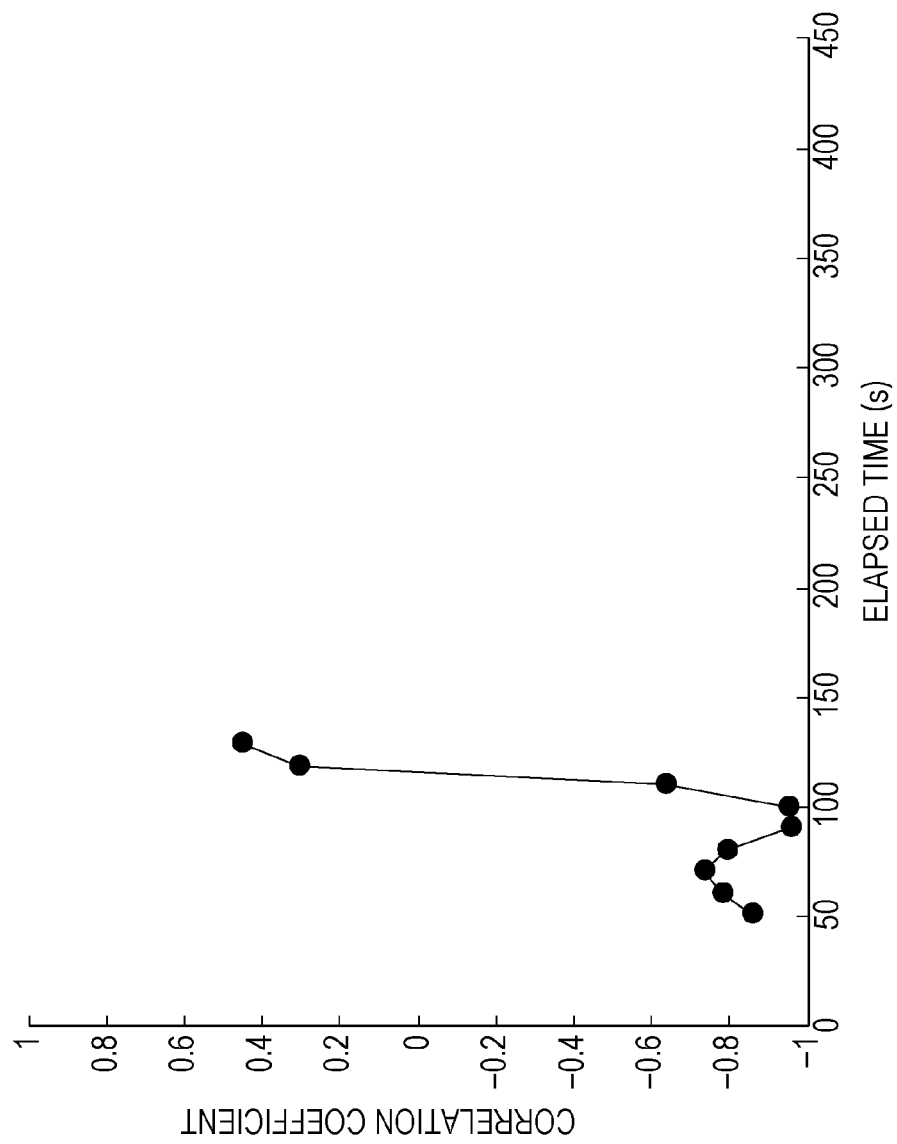
FIG. 12 is a drawing separately depicting experiment results for case B3, which is one of the plurality of cases in FIG. 8.
Figure 13:
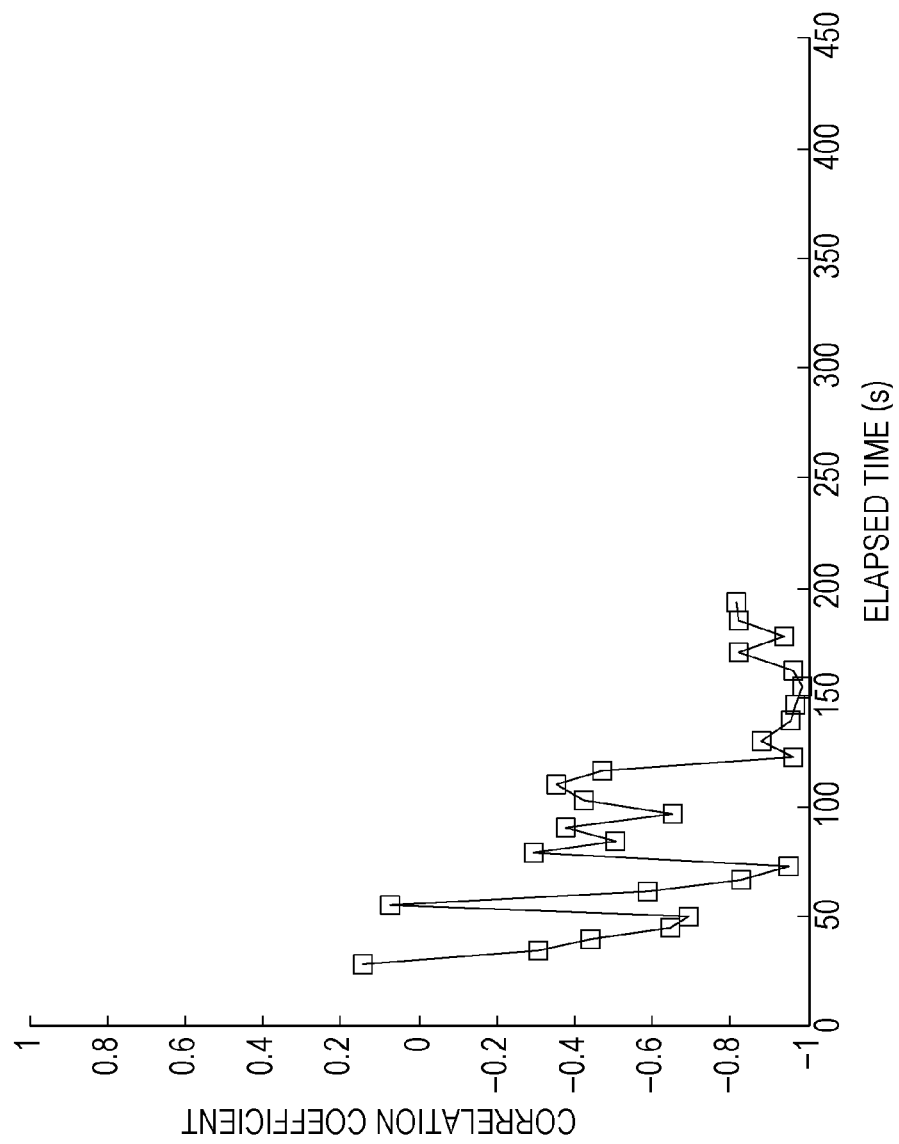
FIG. 13 is a drawing separately depicting experiment results for case A3, which is one of the plurality of cases in FIG. 8.
Figure 14:
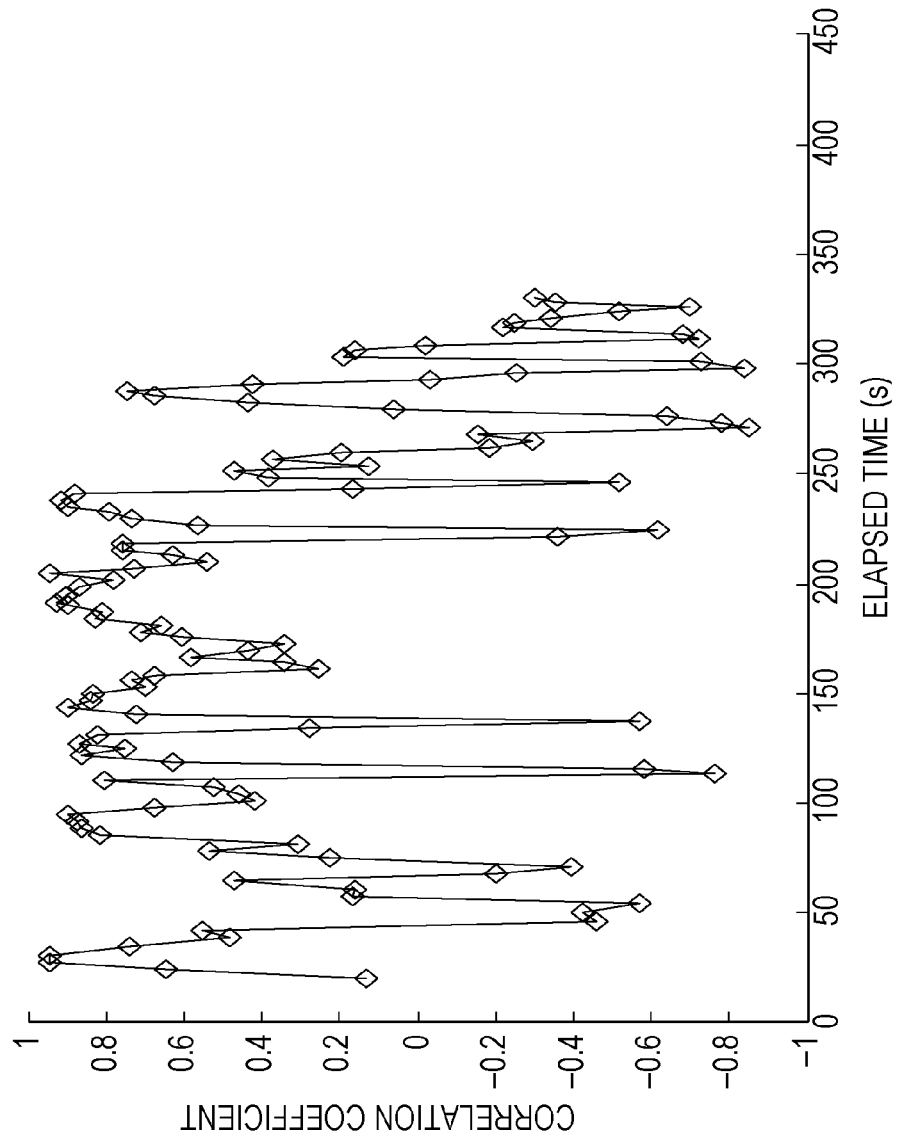
FIG. 14 is a drawing separately depicting experiment results for case A4, which is one of the plurality of cases in FIG. 8.
Figure 15:
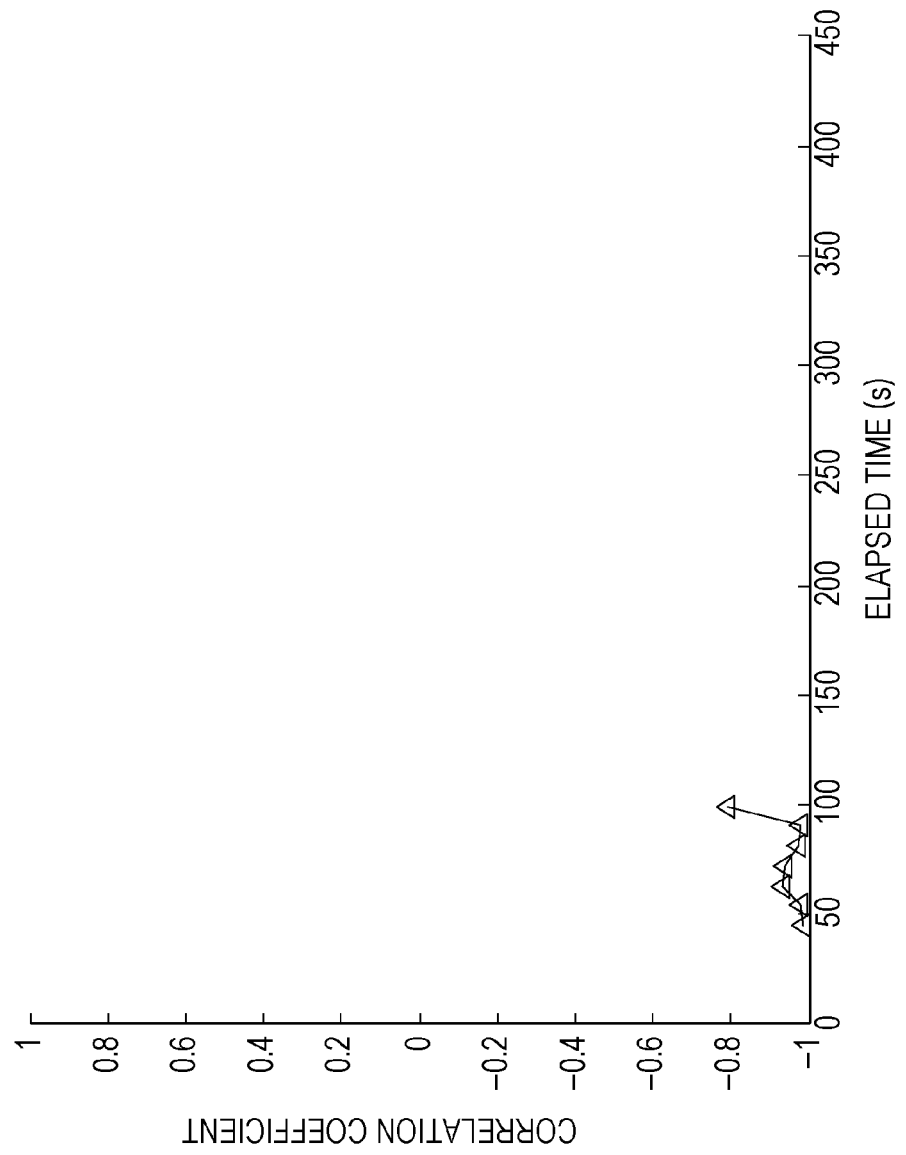
FIG. 15 is a drawing separately depicting experiment results for case B2, which is one of the plurality of cases in FIG. 8.
Figure 16:
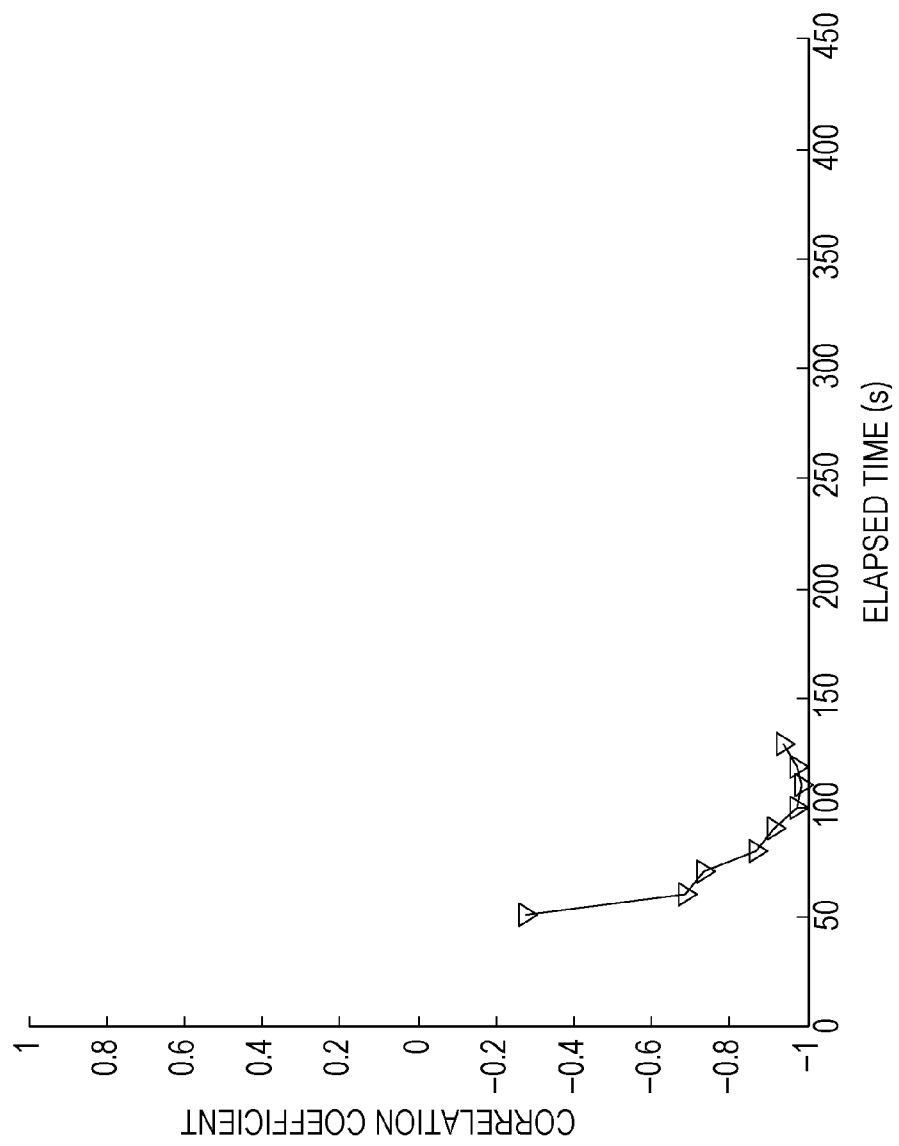
FIG. 16 is a drawing separately depicting experiment results for case B4, which is one of the plurality of cases in FIG. 8.
Figure 17:
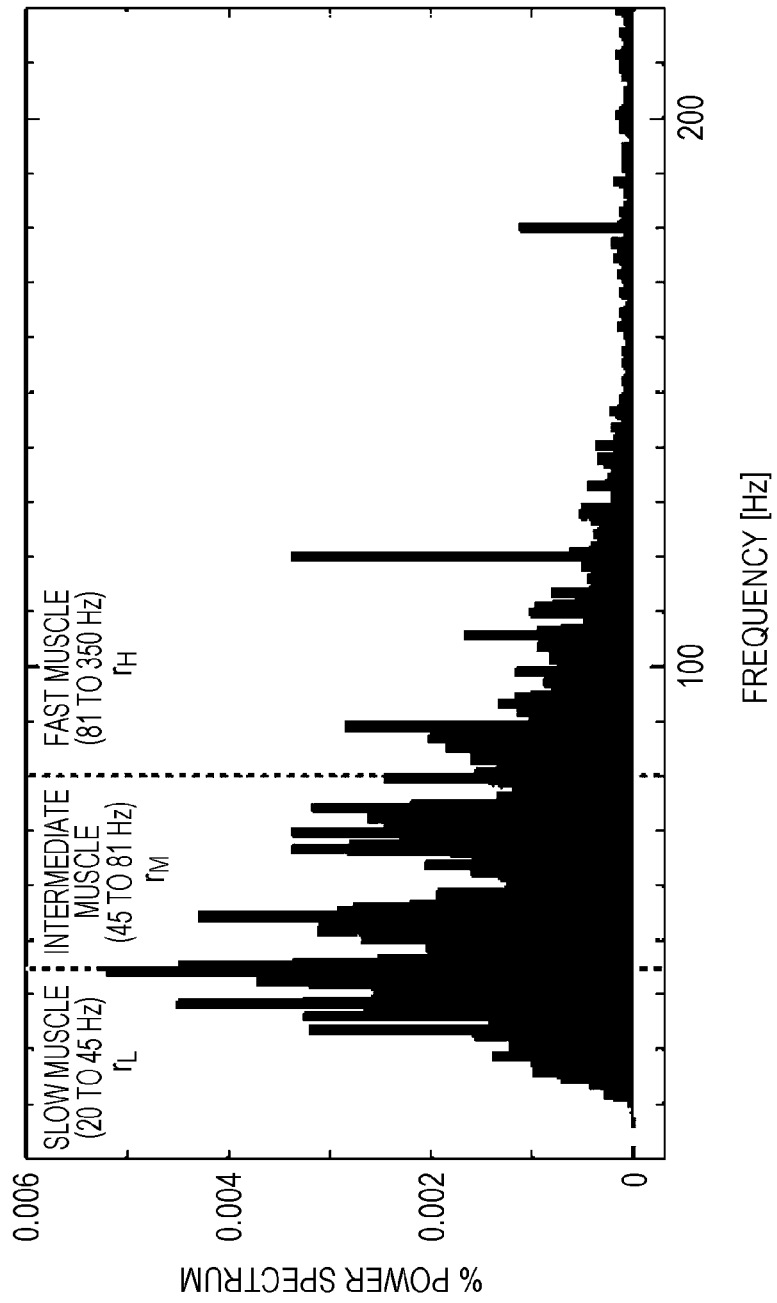
FIG. 17 is a drawing depicting an example of three frequency bands given in Japanese Unexamined Patent Application Publication No. 2015-62658.
Figure 18:
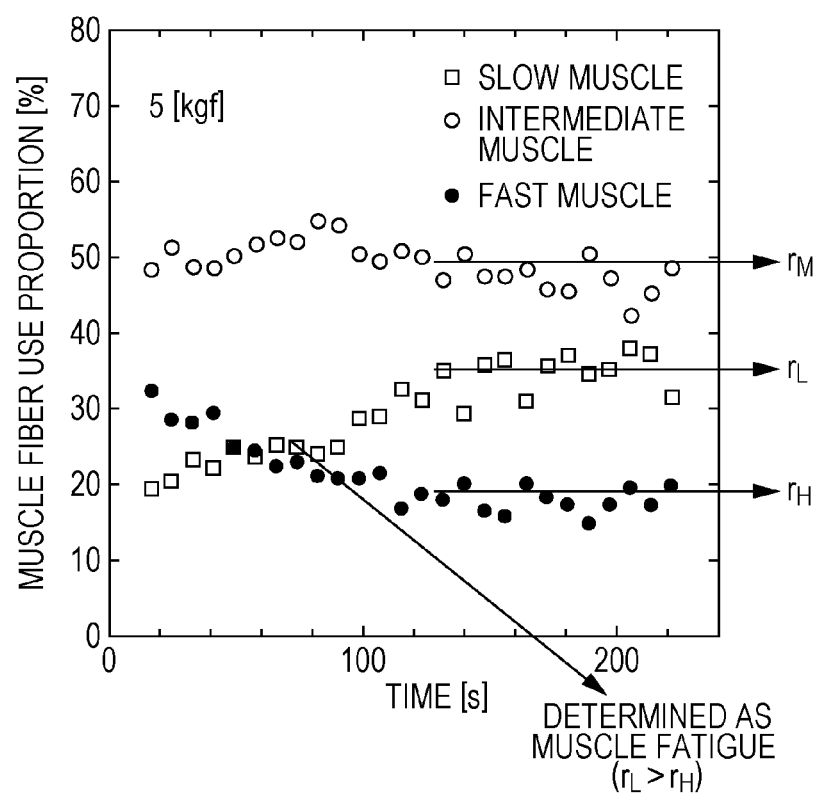
FIG. 18 is a drawing depicting a method for determining muscle fatigue in the method described in Japanese Unexamined Patent Application Publication No. 2015-62658.
Figure 19:
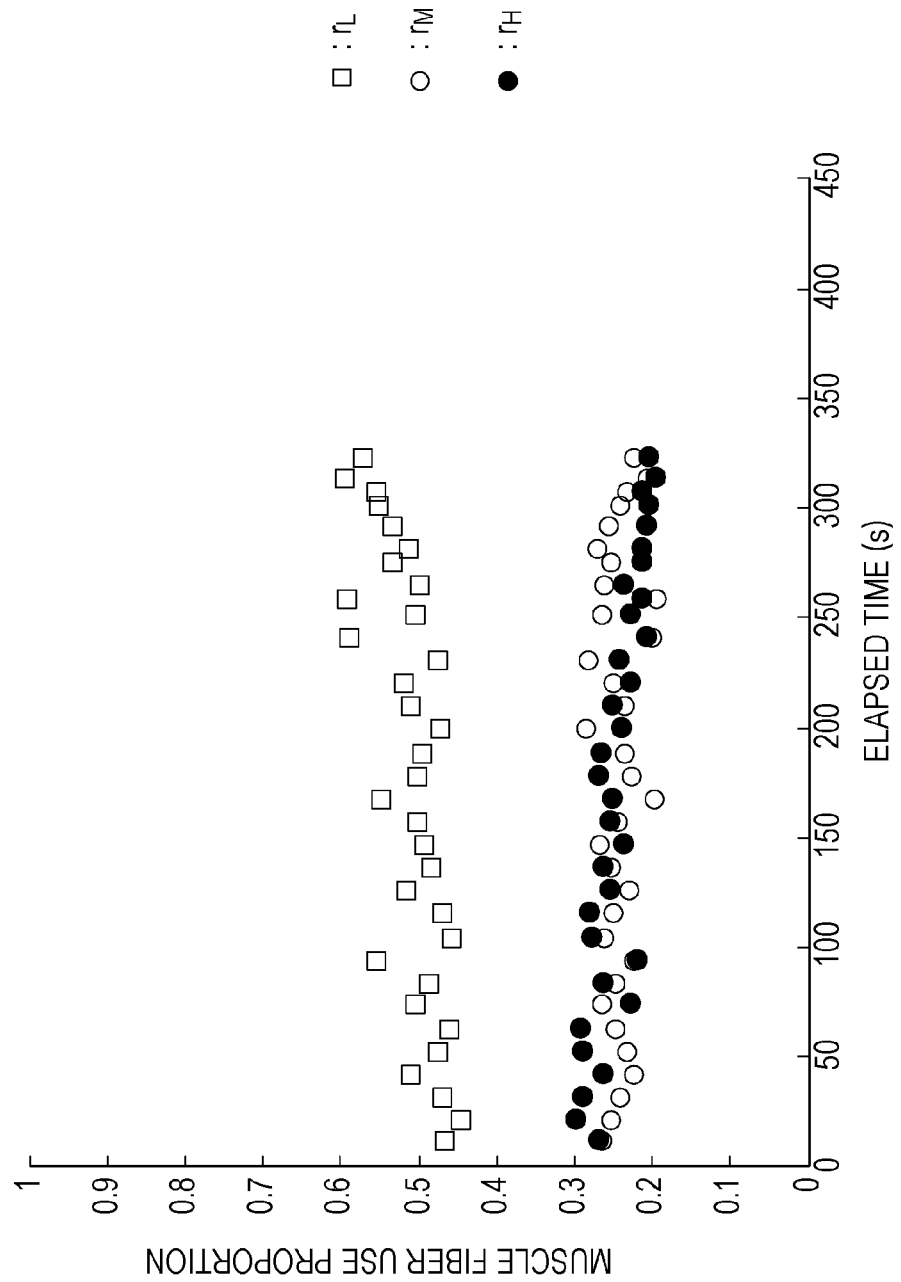
FIG. 19 is a drawing depicting experiment results for case A1, which is one of the plurality of cases of experiments A and B when evaluating muscle fatigue with the method described in Japanese Unexamined Patent Application Publication No. 2015-62658.
Figure 20:
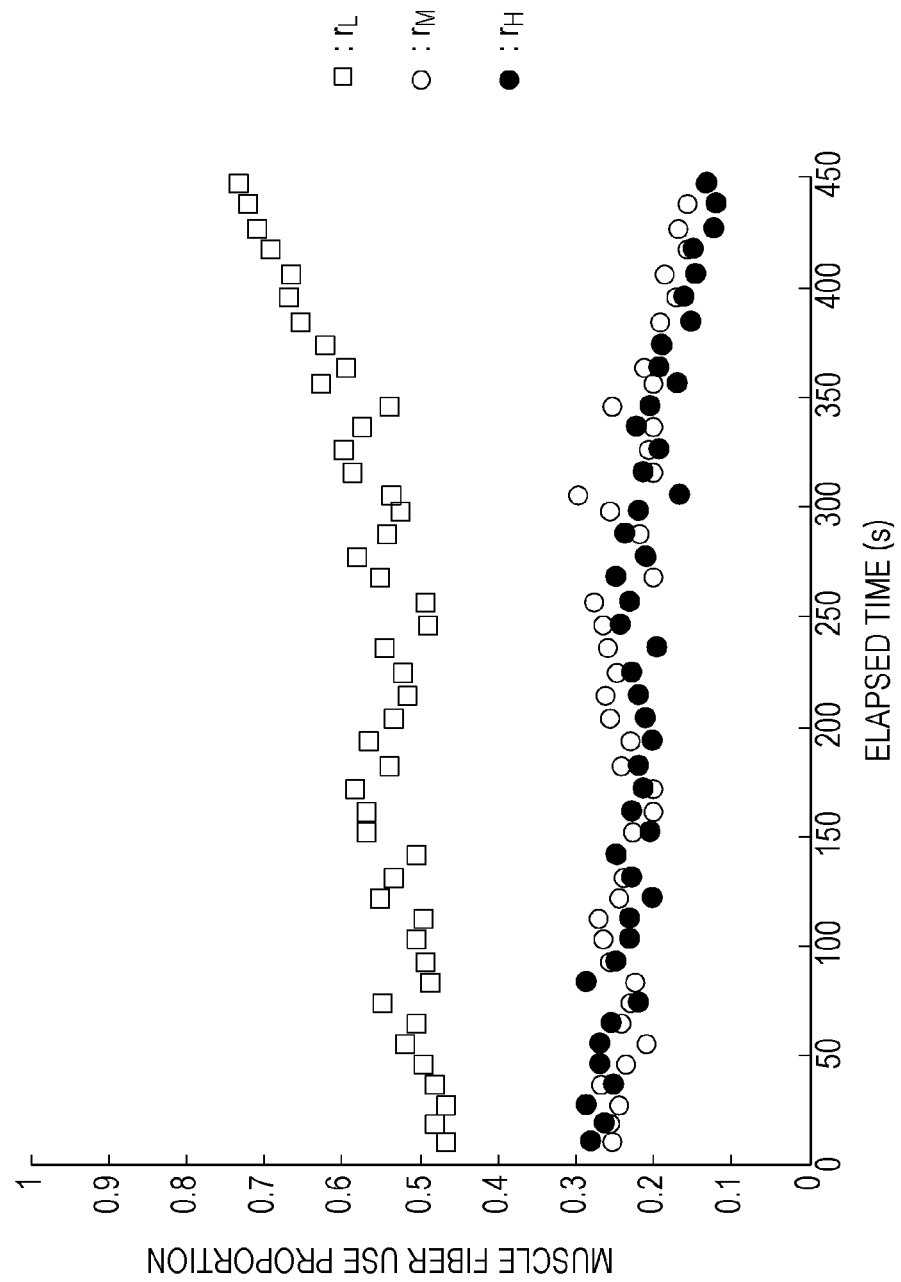
FIG. 20 is a drawing depicting experiment results for case A2, which is one of the plurality of cases of experiments A and B when evaluating muscle fatigue with the method described in Japanese Unexamined Patent Application Publication No. 2015-62658.
Figure 21:
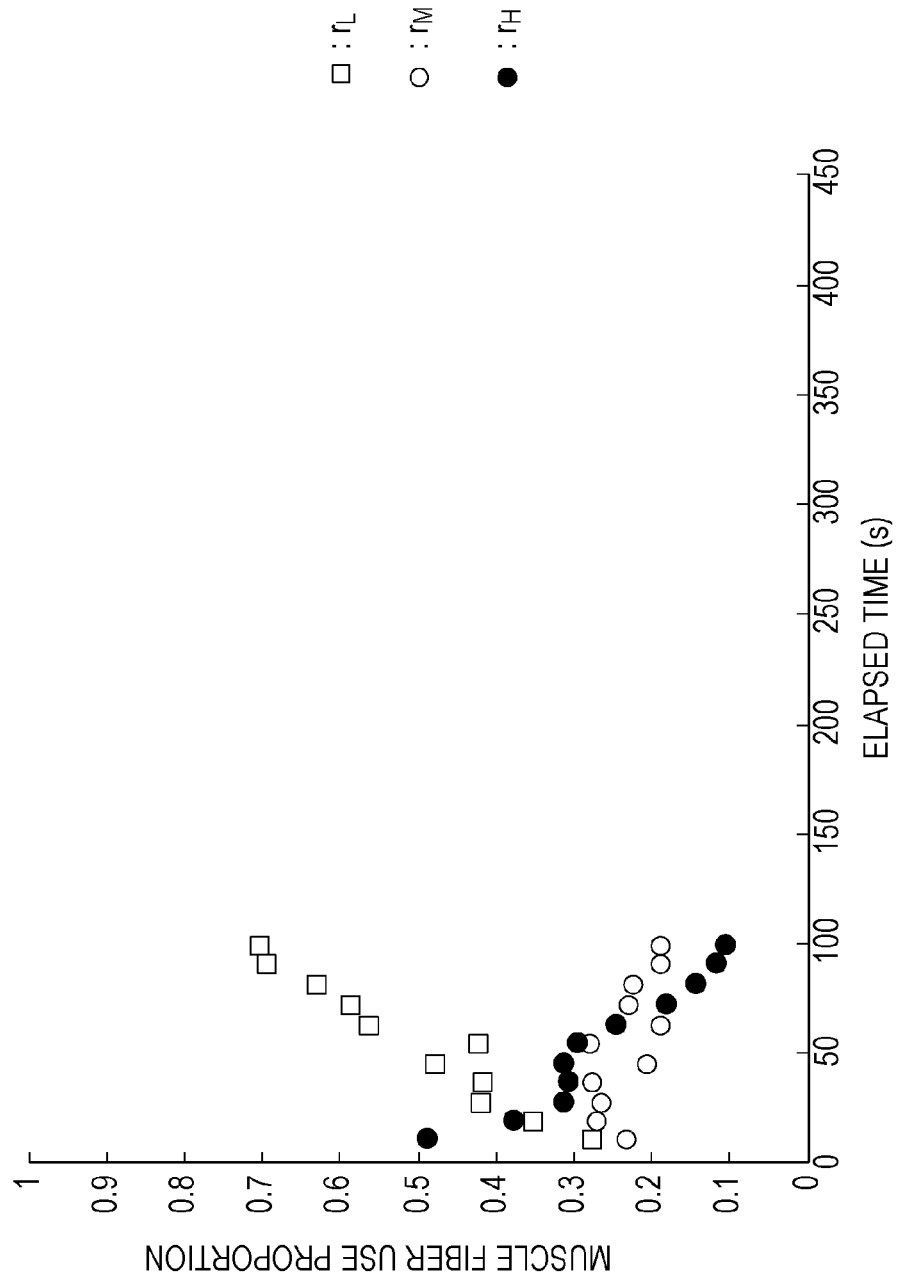
FIG. 21 is a drawing depicting experiment results for case B1, which is one of the plurality of cases of experiments A and B when evaluating muscle fatigue with the method described in Japanese Unexamined Patent Application Publication No. 2015-62658.
Figure 22:
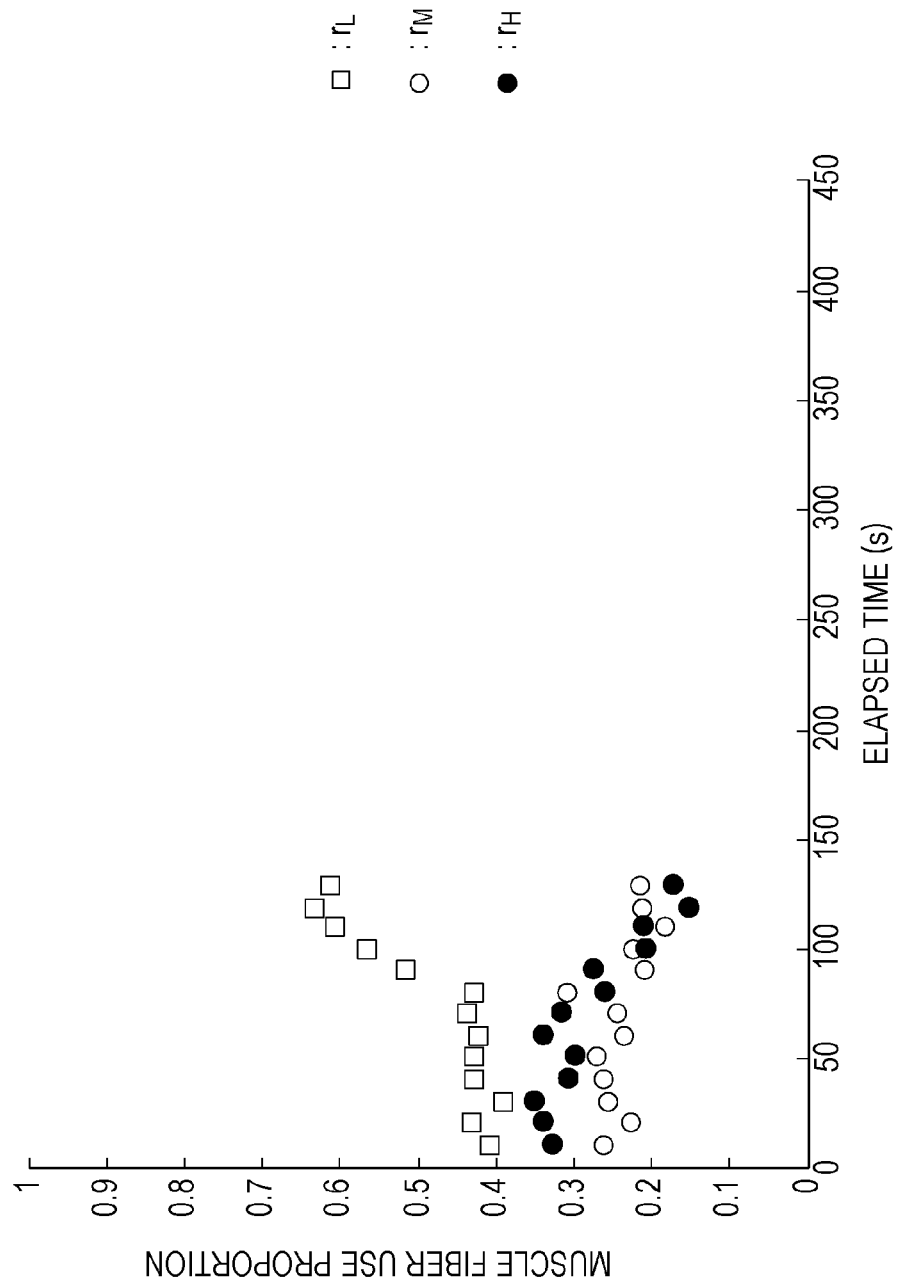
FIG. 22 is a drawing depicting experiment results for case B3, which is one of the plurality of cases of experiments A and B when evaluating muscle fatigue with the method described in Japanese Unexamined Patent Application Publication No. 2015-62658.
Figure 23:
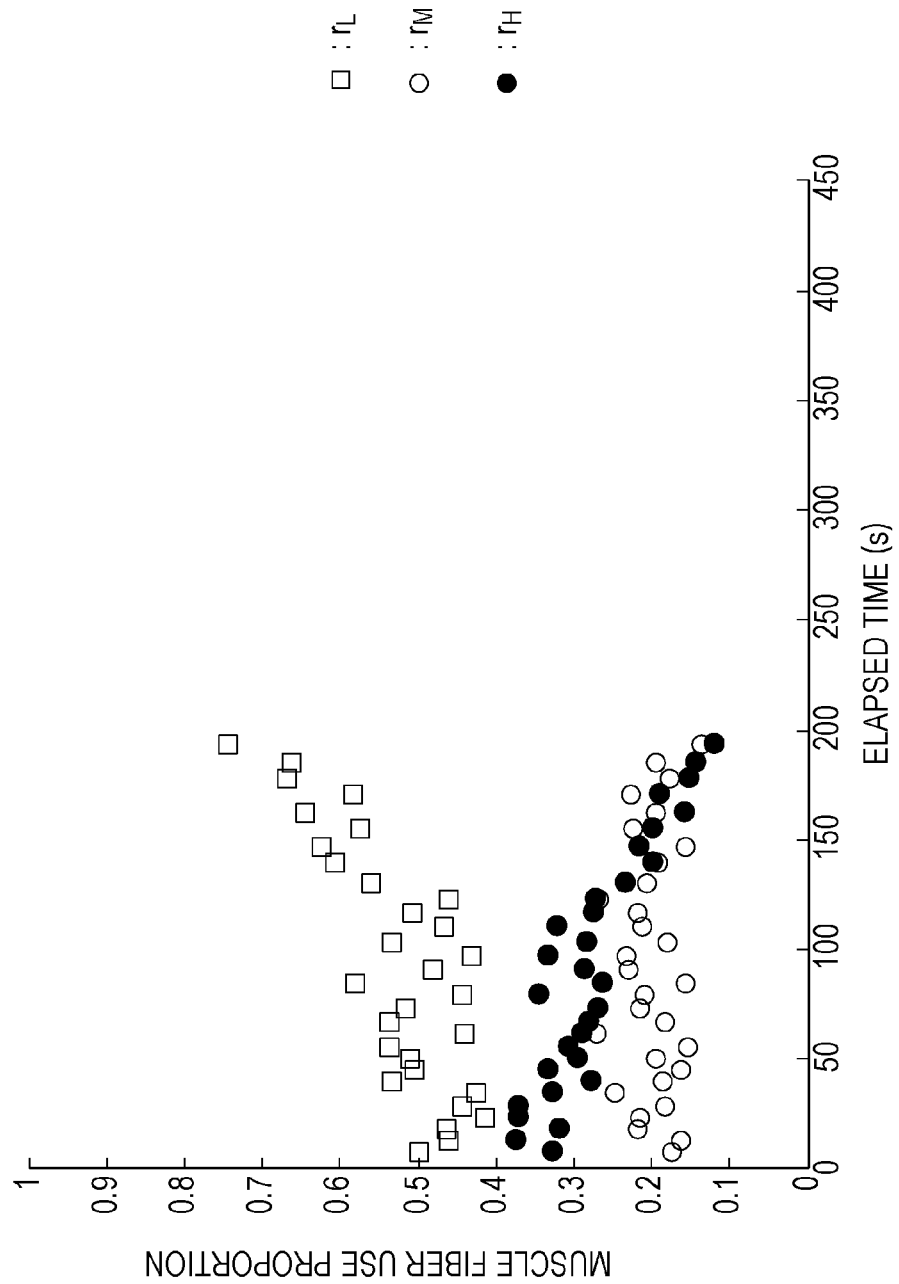
FIG. 23 is a drawing depicting experiment results for case A3, which is one of the plurality of cases of experiments A and B when evaluating muscle fatigue with the method described in Japanese Unexamined Patent Application Publication No. 2015-62658.
Figure 24:
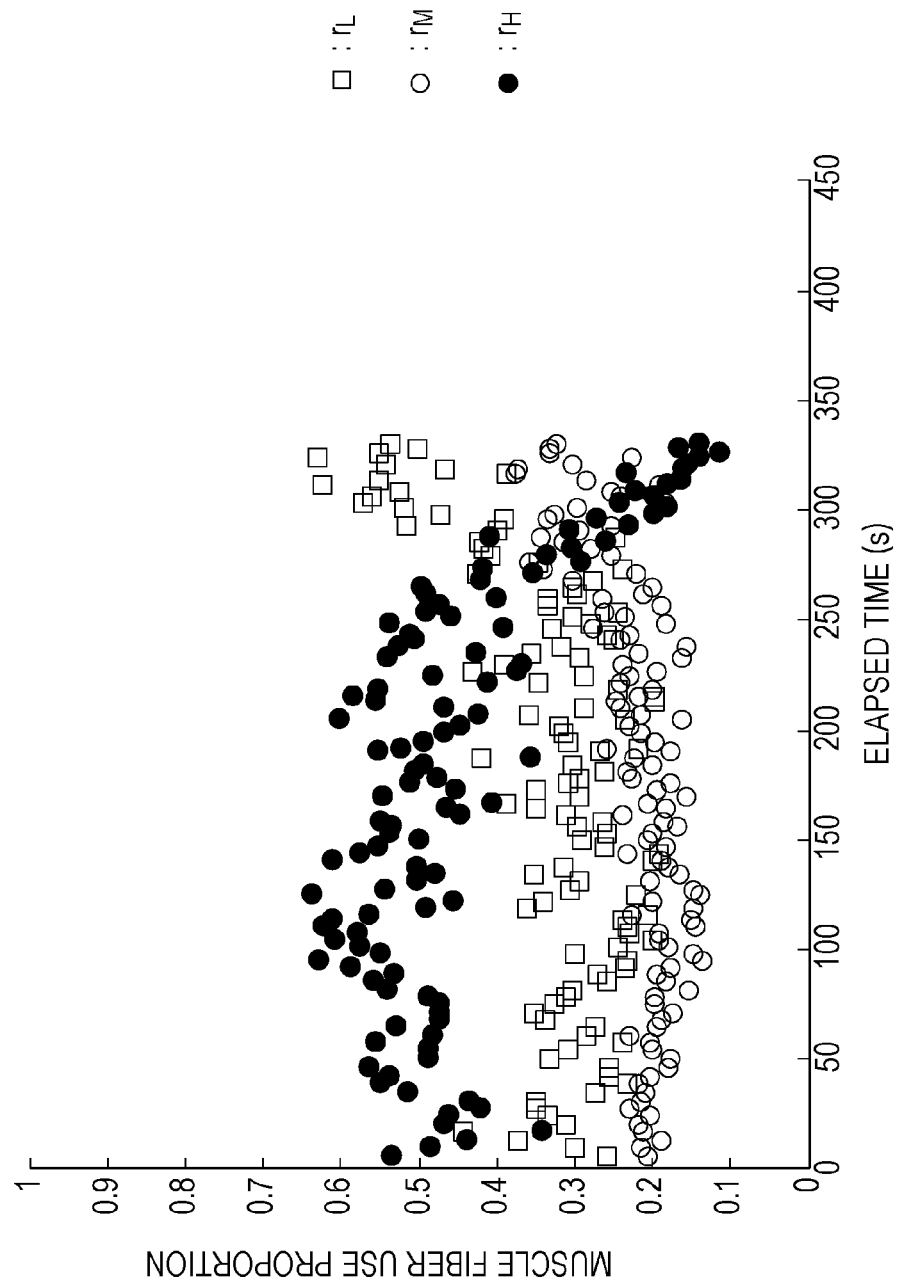
FIG. 24 is a drawing depicting experiment results for case A4, which is one of the plurality of cases of experiments A and B when evaluating muscle fatigue with the method described in Japanese Unexamined Patent Application Publication No. 2015-62658.
Figure 25:
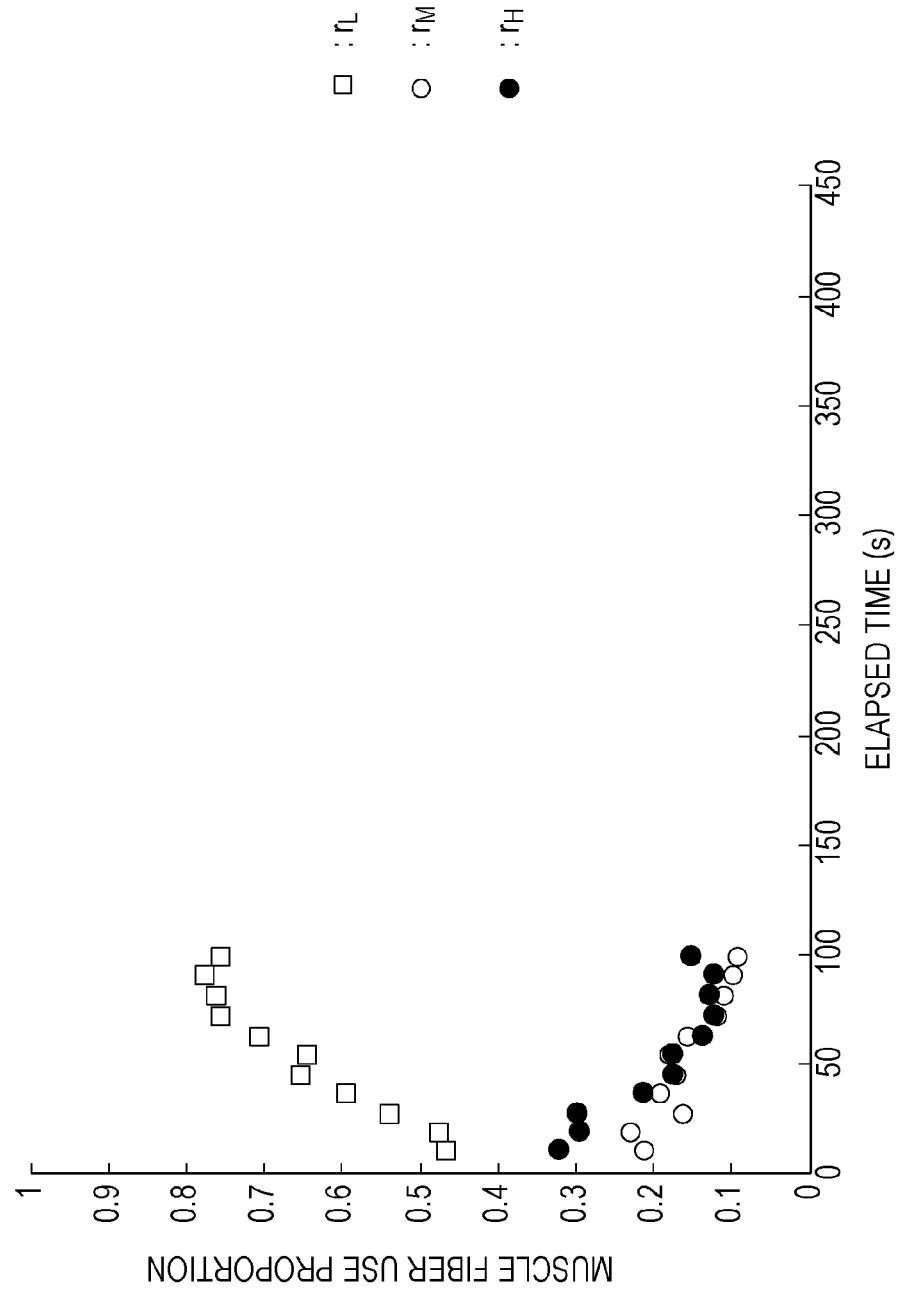
FIG. 25 is a drawing depicting experiment results for case B2, which is one of the plurality of cases of experiments A and B when evaluating muscle fatigue with the method described in Japanese Unexamined Patent Application Publication No. 2015-62658.
Figure 26:
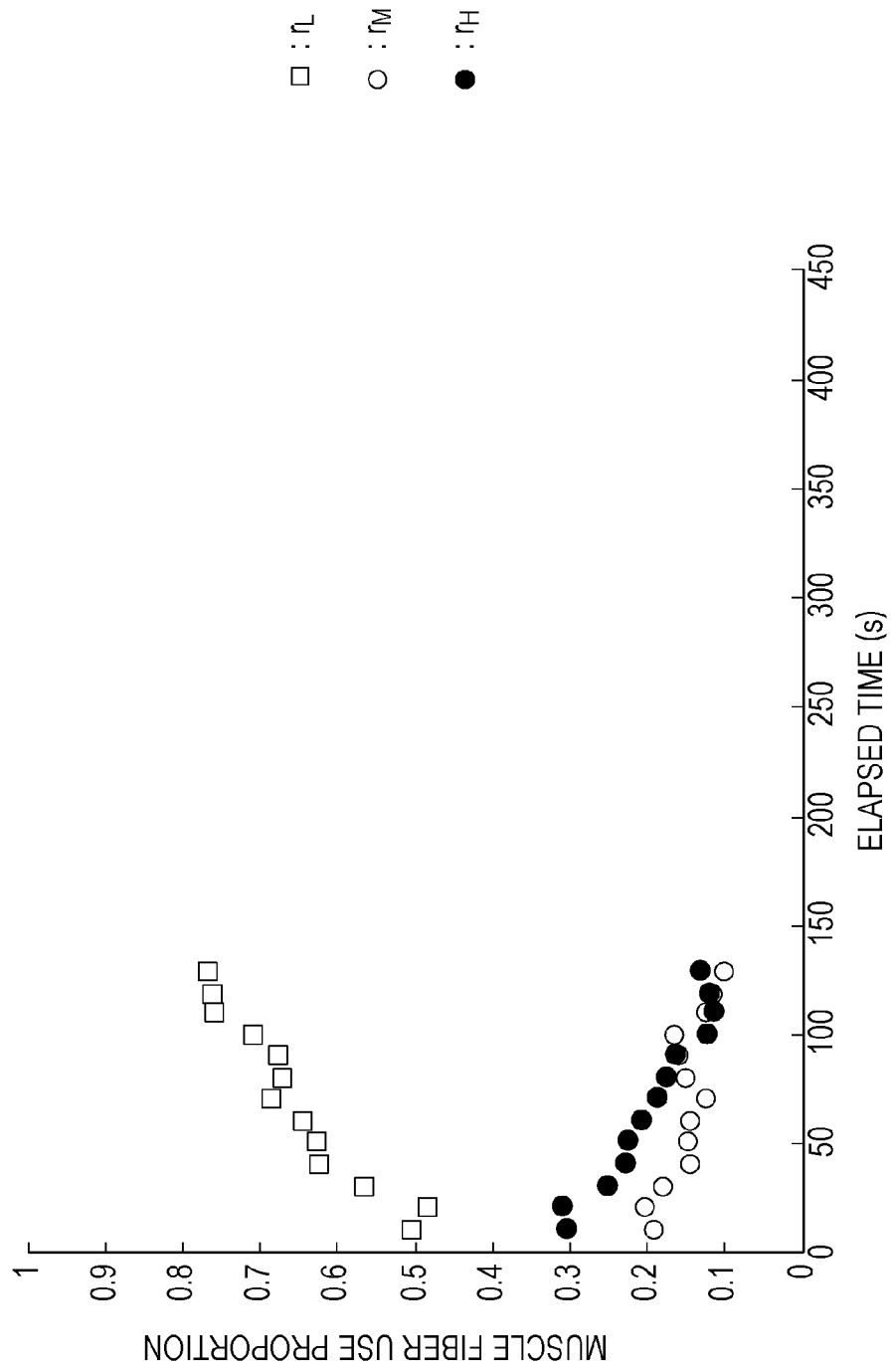
FIG. 26 is a drawing depicting experiment results for case B4, which is one of the plurality of cases of experiments A and B when evaluating muscle fatigue with the method described in Japanese Unexamined Patent Application Publication No. 2015-62658.

Thus, reducing the number of pieces of data for calculating the correlation coefficient is feasible as one means for solving problem 1. For example, FIG. 8 depicts calculation results for the correlation coefficient in cases A1 to A4 and B1 to B4 when the number of pieces of data necessary for calculating the correlation coefficient is reduced from the myoelectric potentials of 120 cycles (5 cycles per frame for 24 frames×5 cycles) to those of 15 cycles (3 cycles per frame for 5 frames×3 cycles). Details of the calculation results for the correlation coefficient in each of cases A1 to A4 and B1 to B4 are separately depicted in FIGS. 9 to 16. When the number of pieces of data for calculating the correlation coefficient is reduced, a new problem occurs in that the correlation coefficient fluctuates considerably and becomes unstable, and it therefore becomes difficult to estimate muscle fatigue. Hereinafter, this problem is referred to as problem 4. It should be noted that in FIGS. 8 to 16, the horizontal axes indicate the elapsed time (unit: seconds) and the vertical axes indicate the correlation coefficient value.

Meanwhile, experiment results for cases A1 to A4 and B1 to B4 when evaluating muscle fatigue with the method described in Japanese Unexamined Patent Application Publication No. 2015-62658 are separately depicted in FIGS. 19 to 26. In the majority of cases A1 to A4 and B1 to B4, $r_L > r_H$ is established immediately after the start of the experiment, and it is therefore determined that the muscle is fatigued from the beginning. Moreover, as disclosed in FIGS. 21 to 22 and FIGS. 25 and 26, there are overlapping portions between the $r_L$, $r_M$, or $r_H$ region for the biceps and the $r_L$, $r_M$, or $r_H$ region for the triceps, and it is therefore difficult to distinguish whether a muscle is fatigued. It should be noted that in FIGS. 19 to 26, the horizontal axes indicate the elapsed time (unit: seconds) and the vertical axes indicate the use proportion of muscle fibers.

Hereinafter, embodiments will be described in a specific manner with reference to the drawings. It should be noted that the embodiments described hereinafter all represent general or specific examples. The numerical values, the shapes, the materials, the constituent elements, the arrangement positions and modes of connection of the constituent elements, the steps, and the order of the steps and the like given in the following embodiments are examples and are not intended to limit the present disclosure. Furthermore, from among the constituent elements in the following embodiments, constituent elements that are not mentioned in the independent claims indicating the most significant concepts are described as optional constituent elements. Furthermore, with regard to notation, ordinal numbers such as first, second, and third may be added, as appropriate, to the constituent elements and the like.

Furthermore, the drawings are schematic views and are not always depicted in an exact manner. In addition, in the drawings, constituent elements that are substantially the same are denoted by the same reference symbols, and there are cases where redundant descriptions are omitted or simplified.

Embodiment 1

(1-1. Muscle Fatigue Output Method)

As a result of investigating various problems such as the aforementioned, the inventors involved in the present disclosure discovered the muscle fatigue output method according to the present embodiment in which a parameter indicating a frequency characteristic and a parameter indicating an amplitude characteristic of myoelectric potentials are used. Hereinafter, the muscle fatigue output method according to the present embodiment will be described.

Specifically, in the present method, the MNF of myoelectric potentials is used as a parameter indicating a frequency characteristic and the ARV of myoelectric potentials is used as a parameter indicating an amplitude characteristic. The inventors involved in the present disclosure also discovered using the ratio between the MNF and ARV of myoelectric potentials as an index for muscle fatigue.

In the muscle fatigue output method according to the present embodiment, MNF/ARV or ARV/MNF constituting the MNF and ARV ratio is calculated over time, and the calculation results are plotted in a graph in which the horizontal axis indicates the elapsed time and the vertical axis indicates the MNF/ARV or ARV/MNF value. It should be noted that both MNF/ARV and ARV/MNF have positive values, and, specifically, the absolute value for MNF/ARV and the absolute value for ARV/MNF are employed. In addition, a baseline for determining whether or not a muscle is fatigued is set in the aforementioned graph. The baseline divides the graph region for the elapsed time and the MNF and ARV ratio into a muscle fatigue determination region and a muscle fatigue non-determination region. When the MNF and ARV ratio is included in the muscle fatigue determination region, for example, when MNF/ARV falls below the baseline, it is determined that the muscle fatigue state is in effect. When the MNF and ARV ratio is included in the muscle fatigue non-determination region or is the same as a value on the baseline, for example, when the MNF/ARV ratio is a value that is equal to or greater than the baseline, it is determined that the muscle fatigue state is not in effect. That is, when MNF/ARV is used as an index, the muscle fatigue state is determined as being in effect when MNF/ARV has fallen below the baseline. Conversely, when ARV/MNF is used as an index, the muscle fatigue state is determined as being in effect if ARV/MNF has exceeded the baseline. In this way, it was discovered that it is possible to determine the muscle fatigue state on the basis of the relationship between the baseline and MNF/ARV or ARV/MNF. In the description hereinafter, it is assumed that MNF/ARV is used as an index.

It should be noted that a median frequency (MDF), which is a frequency median value, may be used besides the MNF as a parameter indicating a frequency characteristic. A root mean square (RMS) may be used besides the ARV as a parameter indicating an amplitude characteristic. The index for muscle fatigue may be the MDF and RMS ratio, the MDF and ARV ratio, or the MNF and RMS ratio.

Here, in the ratio between the parameter indicating the frequency characteristic (MNF or MDF) and the parameter indicating the amplitude characteristic (ARV or RMS), the value used for the denominator is either of the value of the parameter indicating the frequency characteristic or the value of the parameter indicating the amplitude characteristic. The value used for the numerator is the value of the parameter other than that used for the denominator. That is, when the value of the parameter indicating the frequency characteristic is used for the denominator, the value of the parameter indicating the amplitude characteristic is used for the numerator. Alternatively, the inverse thereof is established. The units of the numerator and denominator in the ratio are µV/Hz or Hz/µV. Thus, the ratio may have units. However, in the calculation of the correlation coefficient described in T. Kiryu, I. Sasaki, K. Shibai and K. Tanaka, "Providing Appropriate Exercise Levels for the Elderly" in IEEE Engineering in Medicine and Biology Magazine, vol. 20, no. 6, pp. 116-124, November-December 2001, both MNF and ARV are included in each of the denominator and numerator. Therefore, the correlation coefficient is without units.

Furthermore, the inventors involved in the present disclosure also discovered the following. If the initial MNF/ARV value is low, the load of the exercise for the person is high. In such a case, the time to becoming fatigued decreases, and it is therefore necessary to increase the baseline. On the other hand, if the initial MNF/ARV value is high, the load of the exercise for the person is low. In such a case, the time to becoming fatigued increases, and it is therefore necessary to decrease the baseline.

If the slope of MNF/ARV is steep, the load of the exercise for the person is high. In such a case, the time to becoming fatigued decreases, and it is therefore necessary to increase the baseline. On the other hand, if the slope of MNF/ARV is gentle, the load of the exercise for the person is low. In such a case, the time to becoming fatigued increases, and it is therefore necessary to decrease the baseline.

Figure 27:
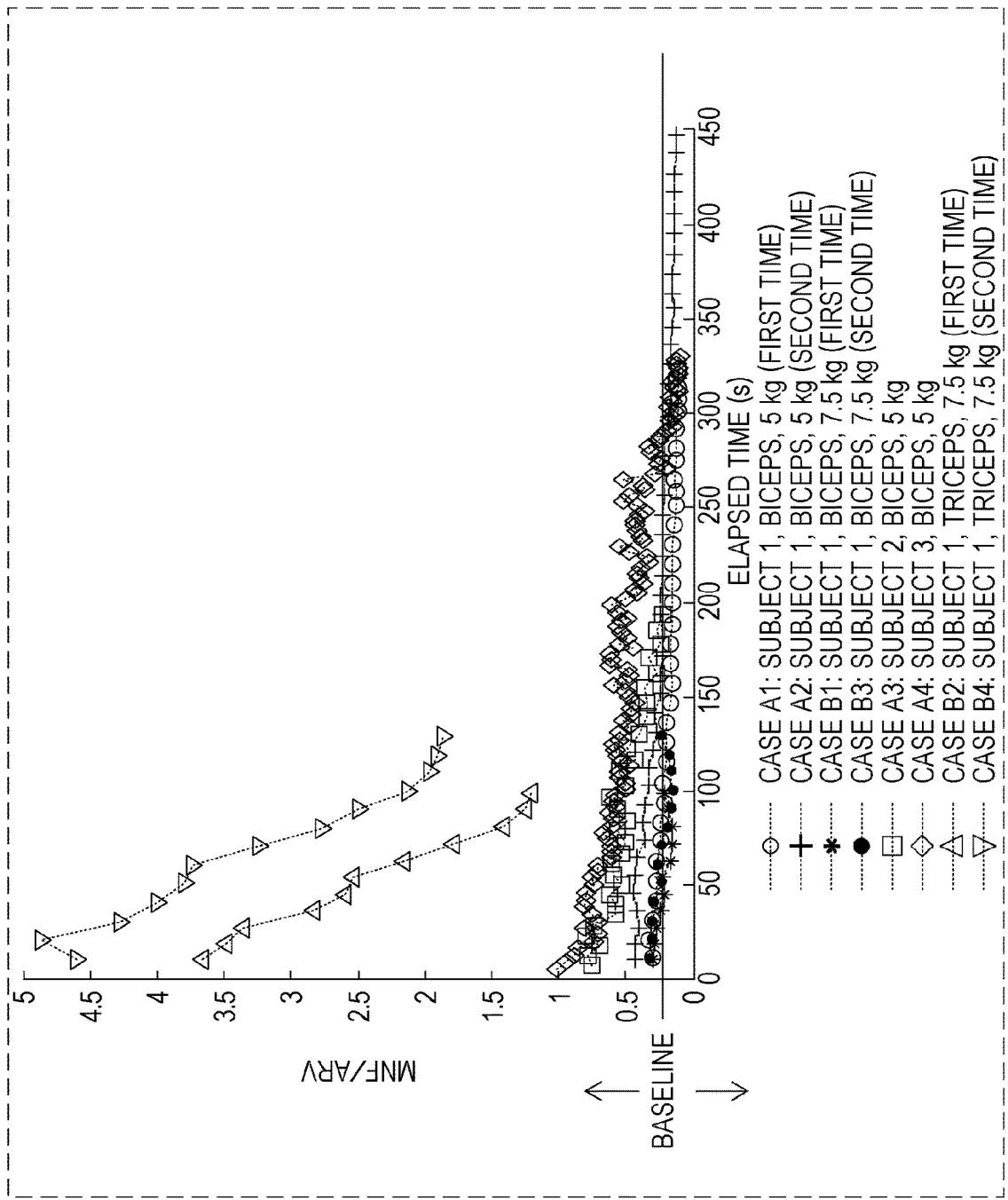
FIG. 27 is a drawing depicting results for experiments A and B when evaluating muscle fatigue with a muscle fatigue output method according to embodiment 1 using MNF/ARV as a muscle fatigue index.
Figure 28:
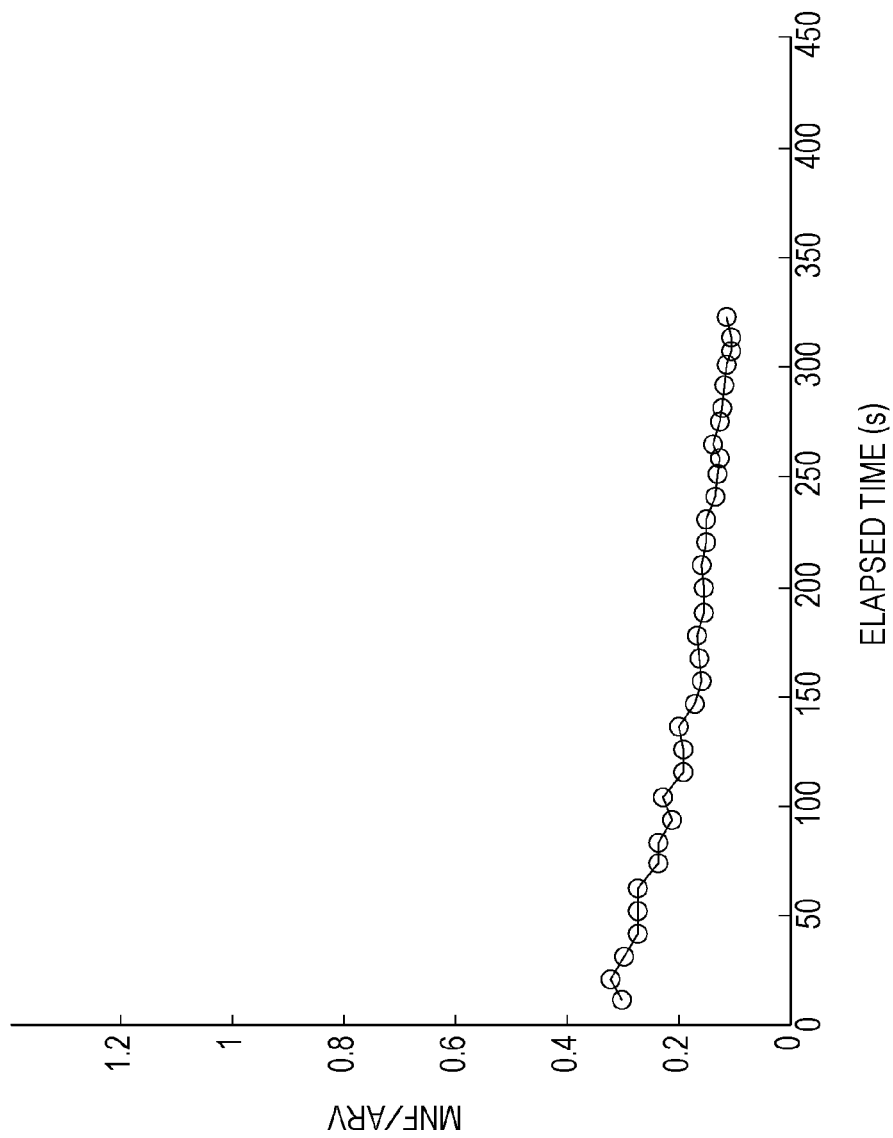
FIG. 28 is a drawing separately depicting experiment results for case A1, which is 1 of the plurality of cases in FIG. 27.
Figure 29:
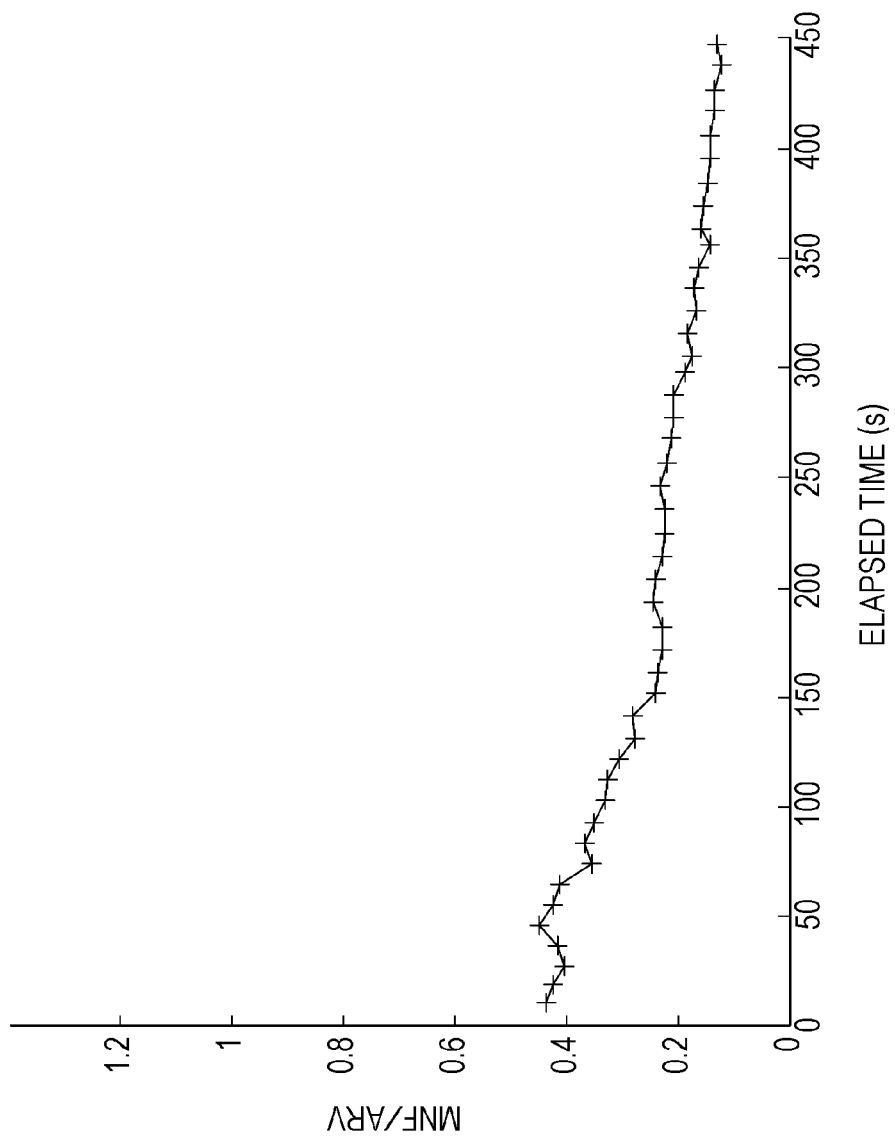
FIG. 29 is a drawing separately depicting experiment results for case A2, which is one of the plurality of cases in FIG. 27.
Figure 30:
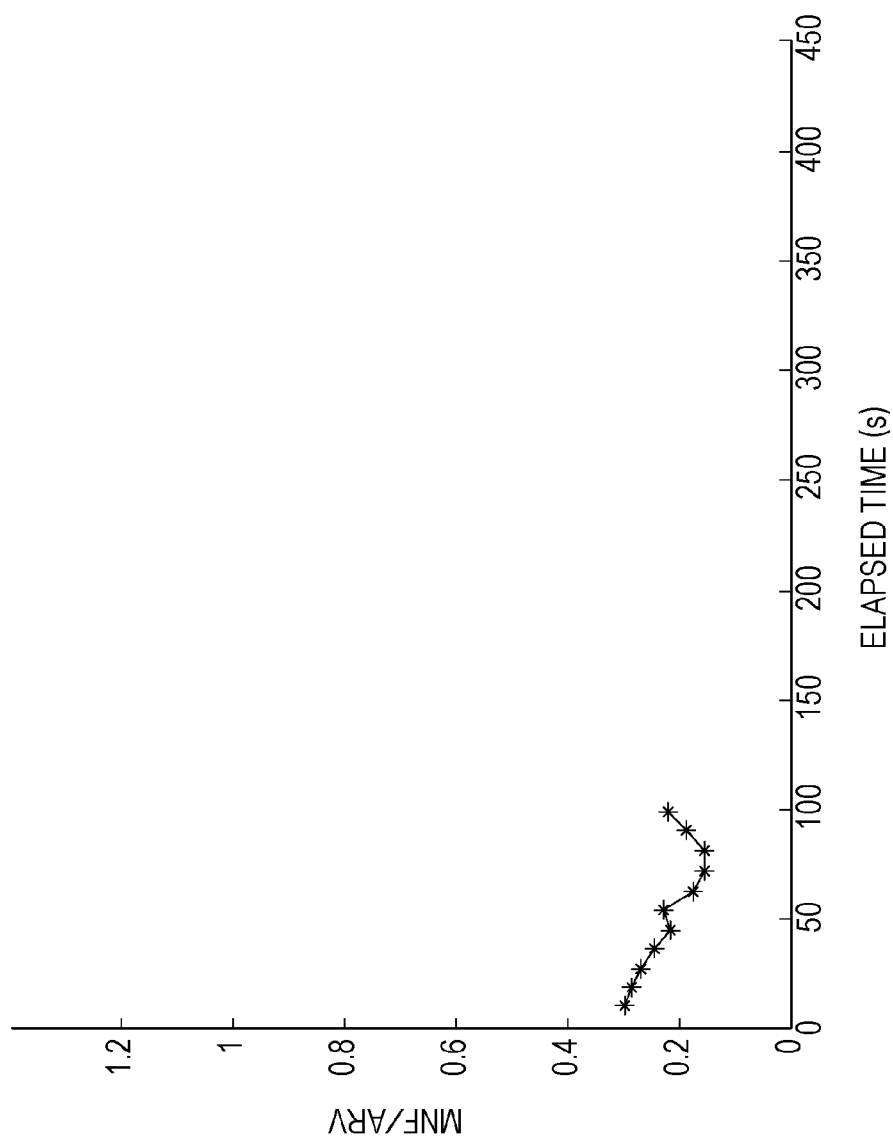
FIG. 30 is a drawing separately depicting experiment results for case B1, which is one of the plurality of cases in FIG. 27.
Figure 31:
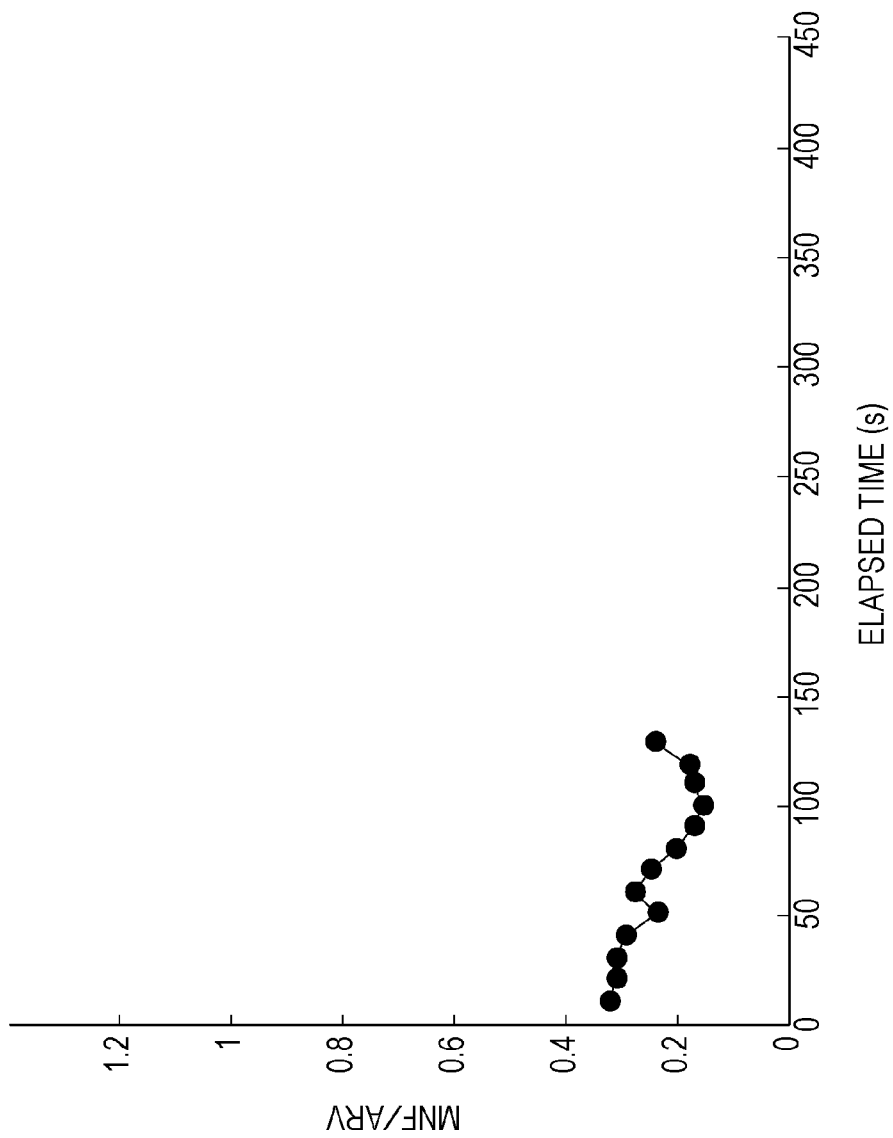
FIG. 31 is a drawing separately depicting experiment results for case B3, which is one of the plurality of cases in FIG. 27.
Figure 32:
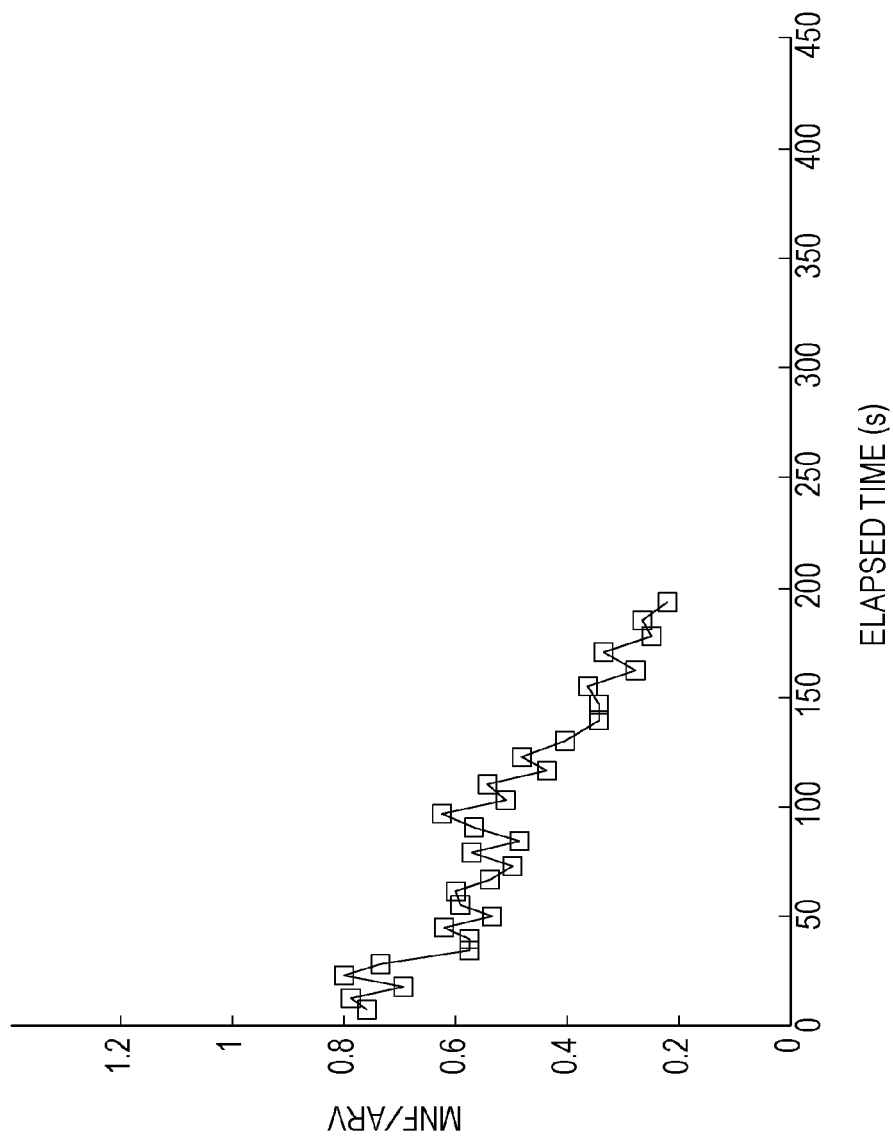
FIG. 32 is a drawing separately depicting experiment results for case A3, which is one of the plurality of cases in FIG. 27.
Figure 33:
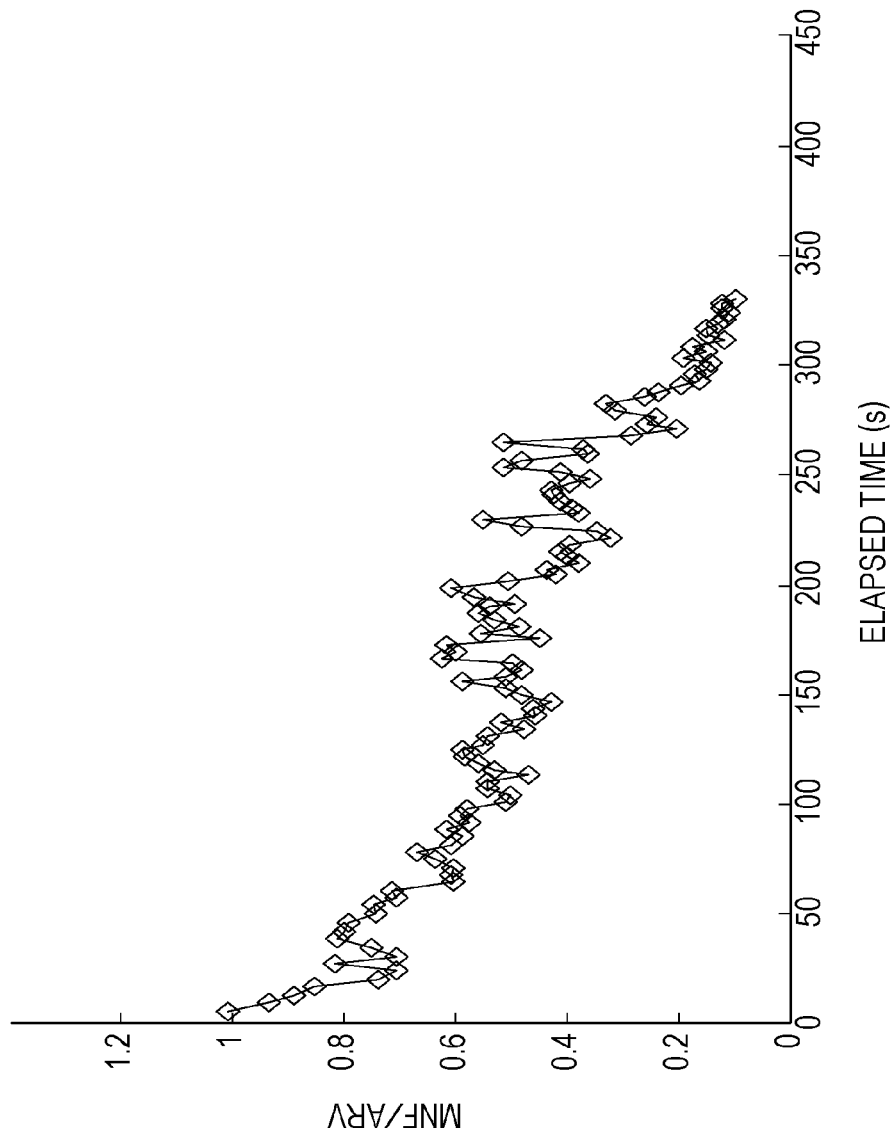
FIG. 33 is a drawing separately depicting experiment results for case A4, which is one of the plurality of cases in FIG. 27.
Figure 34:
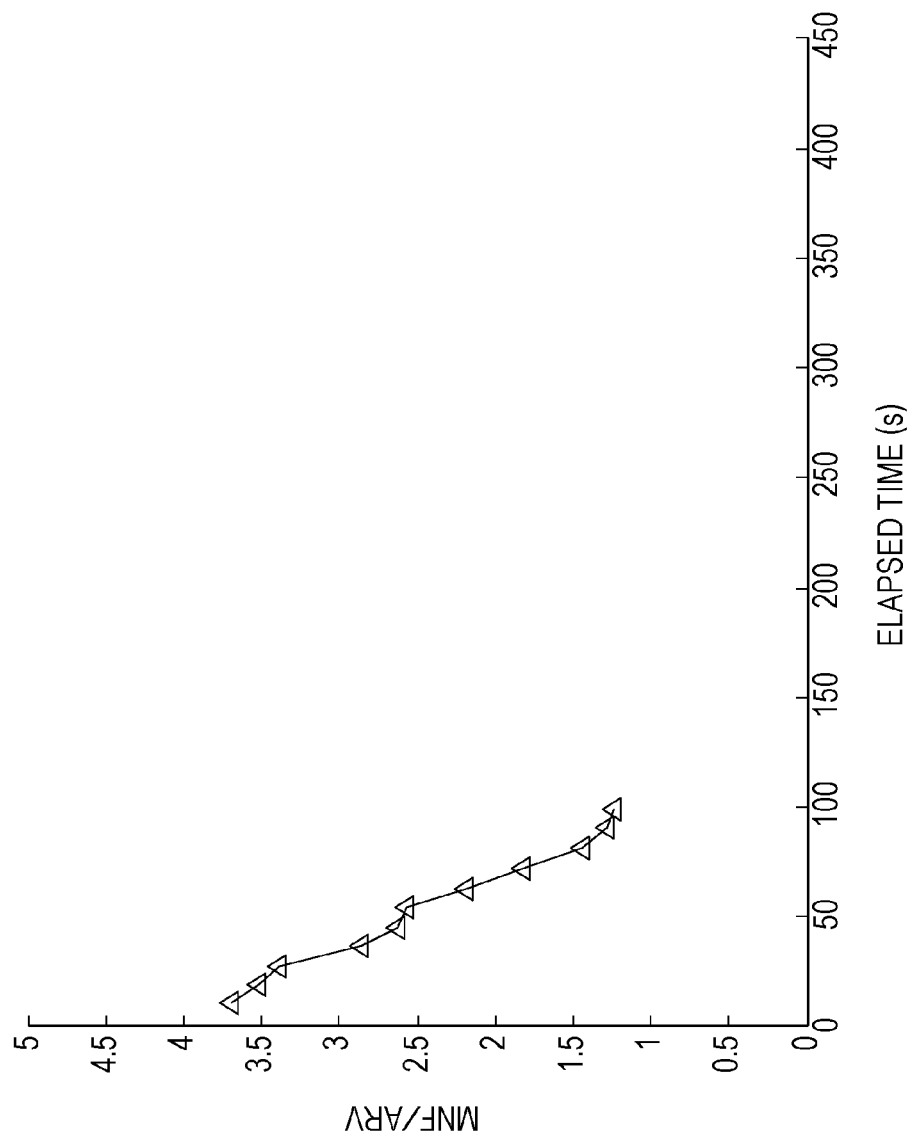
FIG. 34 is a drawing separately depicting experiment results for case B2, which is one of the plurality of cases in FIG. 27.
Figure 35:
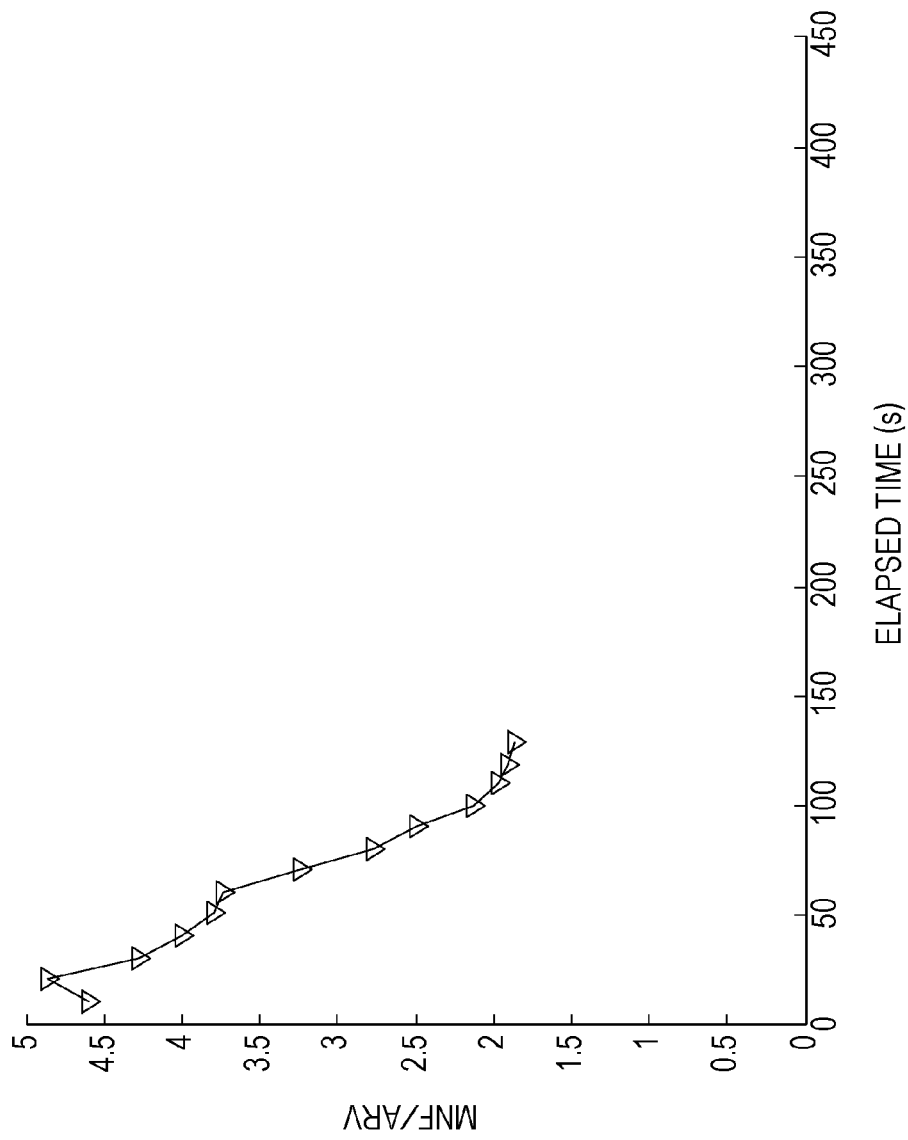
FIG. 35 is a drawing separately depicting experiment results for case B4, which is one of the plurality of cases in FIG. 27.

FIG. 27 is a drawing in which the results of calculating MNF/ARV over time are plotted on a graph with respect to the experiment data of the aforementioned cases A1 to A4 and B1 to B4, on which the horizontal axis indicates elapsed time (unit: seconds) and the vertical axis indicates the MNF/ARV value. That is, FIG. 27 is a drawing depicting results for experiments A and B when evaluating muscle fatigue with a muscle fatigue output method according to the present embodiment using MNF/ARV as a muscle fatigue index. In FIG. 27, the myoelectric potentials of three cycles serve as one frame, and MNF/ARV calculated in each one frame using the myoelectric potentials in each frame is plotted in association with elapsed time. It should be noted that in FIG. 27, the frames are set in such a way as to shift one frame at a time and to not overlap with each other; however, the frames may be set in such a way that, within each frame, one cycle or two cycles overlap.

Figure 36:
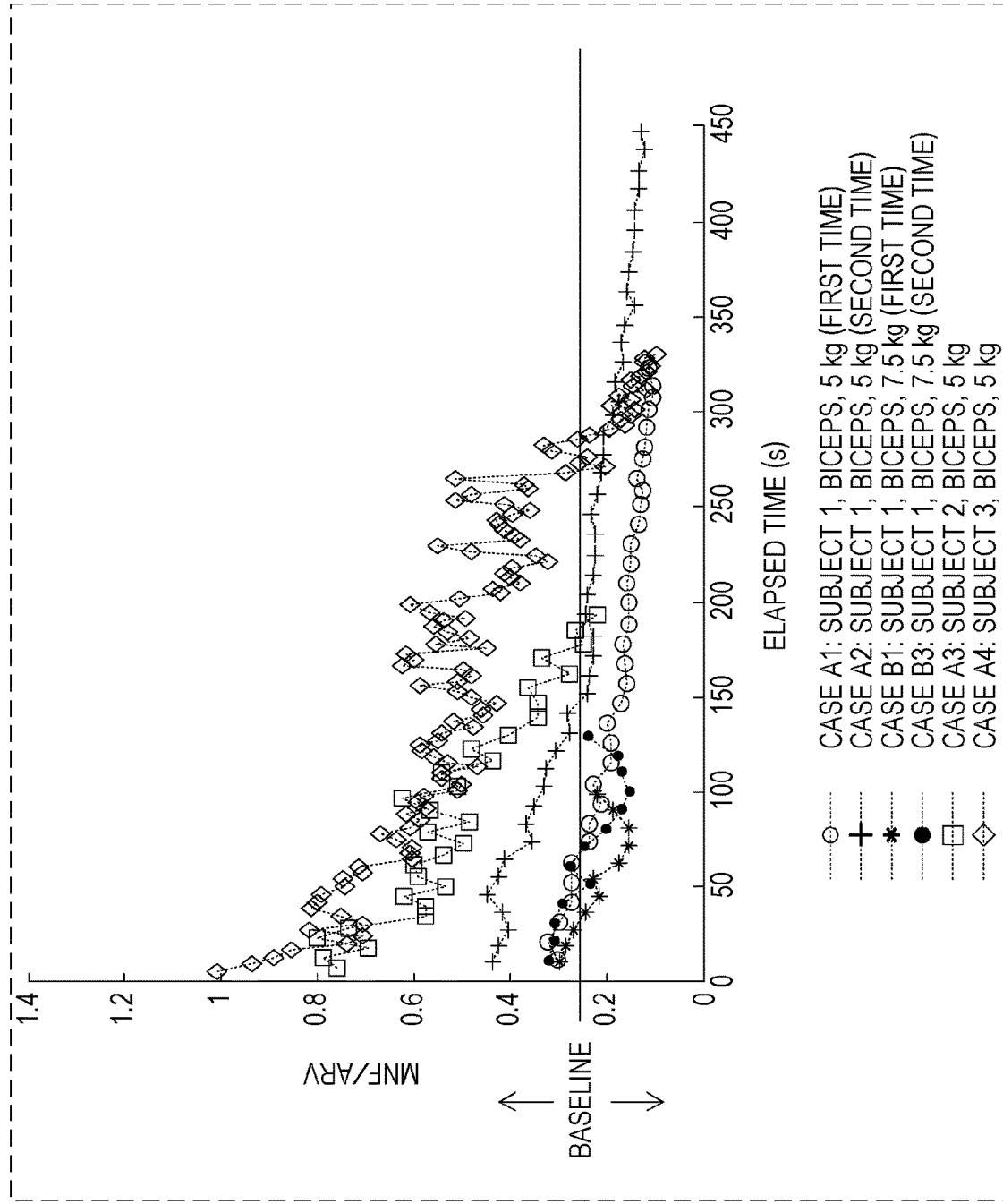
FIG. 36 is a drawing depicting experiment results for a muscle fatigue index when outputting information regarding muscle fatigue in the muscle fatigue output method according to embodiment 1.

Details of cases A1 to A4 and B1 to B4 are separately depicted in FIGS. 28 to 35. FIG. 36 depicts MNF/ARV for cases A1 to A4, B1, and B3 relating to the biceps. The range of MNF/ARV for the triceps corresponding to cases B2 and B4 is different from the range of MNF/ARV for the biceps corresponding to cases A1 to A4, B1, and B3, and the value of the range of MNF/ARV for the triceps is considerably larger than the value of the range of MNF/ARV for the biceps. Therefore, the range of MNF/ARV for the triceps ordinarily exceeds the baseline, which is set at a position intersecting the range of MNF/ARV for the biceps, and it can be evaluated that the triceps muscle is not fatigued. Furthermore, when MNF/ARV for the biceps falls below the baseline, it can be evaluated that the biceps muscle has fatigued.

Furthermore, as mentioned above, for the biceps, the way in which MNF/ARV appears is different depending on the subject and the weight of the load, and it is therefore necessary for the baseline value to not be uniform and to be adjusted.

To determine the baseline value, after measurement of myoelectric potentials has started, that is, after the experiment for each case has started, the MNF/ARV value that is first output (the initial value) may be used. For example, if the initial value for MNF/ARV is large, the baseline value is decreased. Conversely, if the initial value for MNF/ARV is small, the baseline value is increased.

The baseline can be determined with respect to the aforementioned experiment data by being calculated using expression (1) below. It should be noted that the "initial value" included in expression (1) is the aforementioned initial MNF/ARV value.

$$\text{Baseline} = 1/(a \times \text{initial value} + b) \qquad \text{Expression (1)}$$

a and b are coefficients. The calculation results for the baseline in cases A1 to A4 and B1 to B4 when the values of a and b are respectively 0.2198 and 3.9291 are depicted in FIG. 43. It should be noted that the values of a and b for determining the baseline can be obtained for each individual person or statistically from data obtained at the point in time when a person has performed exercises such as those in experiments A and B and has felt muscle fatigue.

Additionally, to determine the baseline value, after measurement of myoelectric potentials has started, that is, after the experiment for each case has started, the slope of MNF/ARV within an initial predetermined period, namely within a first predetermined time, may be used. The length of the first predetermined time may be changed according to the weight of the load. For example, the length of the predetermined time is reduced as the weight of the load increases. Specifically, the first predetermined time is set to 75 s (seconds) when the weight of the load is 5 kg, and the first predetermined time is set to 37.5 s (seconds) when the weight of the load is 7.5 kg. The relationship between MNF/ARV data within the initial first predetermined time and the time corresponding to MNF/ARV, namely the elapsed time, is linearly approximated, and the values of the slope and intercept of the obtained approximation equation are used to calculate the baseline. It should be noted that a predetermined time for obtaining MNF/ARV may be set during an experiment.

The baseline can be determined with respect to the aforementioned experiment data by being calculated using the expression (2) below. It should be noted that the "slope" and "intercept" included in expression (2) are values for the slope and intercept of an approximation equation obtained by linearly approximating the relationship between MNF/ARV data within the initial first predetermined time and the time corresponding to MNF/ARV.

$$\text{Baseline} = 1/(c \times \text{slope} + d \times \text{intercept} + e) \qquad \text{Expression (2)}$$

c, d, and e are coefficients. The calculation results for the baseline in cases A1 to A4 and B1 to B4 when the values of c, d, and e are respectively −10.6575, 0.1614, and 3.9159 are depicted in FIG. 44. It should be noted that the values of c, d, and e for determining the baseline can be obtained for each individual person or statistically from data obtained at the point in time when a person has performed exercises such as those in experiments A and B and felt muscle fatigue.

It should be noted that in order to cope with fluctuations in MNF/ARV corresponding to an individual person, it may be determined that the muscle fatigue state is in effect when MNF/ARV has fallen below the baseline and has then either continued to remain below the baseline for a second predetermined time constituting a predetermined period or has fallen below the baseline a predetermined number of times. The second predetermined time and the aforementioned predetermined number of times may be determined on the basis of the initial value for MNF/ARV. For example, if the initial value for MNF/ARV is large, the second predetermined time is increased and the predetermined number of times is increased. The time during which counting is performed for the predetermined number may be restricted or may not be restricted. Furthermore, in the case where it is counted that MNF/ARV has fallen below the baseline and then MNF/ARV does not fall below the baseline for at least a third predetermined time constituting a predetermined period, the entirety or a portion of the count up to that point in time may be nullified, namely reset.

Furthermore, the second predetermined time and the predetermined number of times may be determined according to the baseline value. For example, if the baseline is large, the second predetermined time is increased and the predetermined number of times is increased.

It should be noted that when determining the baseline, the determination method using the aforementioned expression (1) and the determination method using the aforementioned expression (2) may be jointly used. For example, a baseline value calculated using expression (1) and a baseline value calculated using expression (2) may be compared and either thereof selected.

Figure 37:
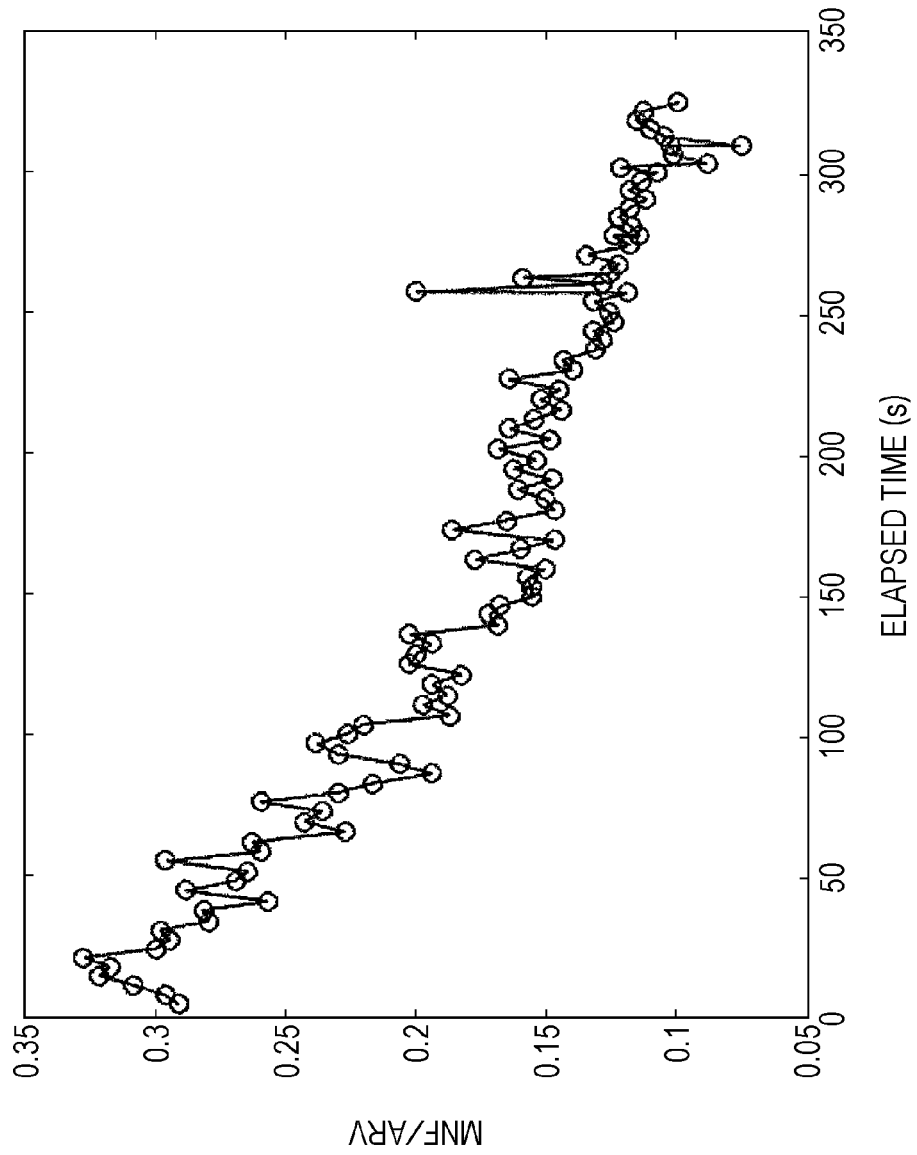
FIG. 37 is a drawing depicting an example of a muscle fatigue index obtained when the calculation method is changed, in the muscle fatigue output method according to embodiment 1.

Furthermore, FIG. 37 depicts a drawing in which values for MNF/ARV, obtained when MNF/ARV is calculated over time for each myoelectric potential of one cycle, are plotted on a graph for case A1. That is, in the example of FIG. 37, MNF/ARV is calculated using the myoelectric potentials of one cycle, whereas in the examples of FIGS. 27 and 28, MNF/ARV is calculated using the myoelectric potentials of three cycles. In the case of FIG. 37, MNF/ARV exhibits a tendency to decrease as time elapses, similar to the case of FIG. 28. Thus, even when MNF/ARV is calculated for each myoelectric potential of one cycle, it is possible to evaluate muscle fatigue using a method similar to the aforementioned. Consequently, the number of cycles of myoelectric potentials applied to calculate MNF/ARV may be of any quantity.

(1-2. Configuration of Muscle Fatigue Output Device)

Figure 38:
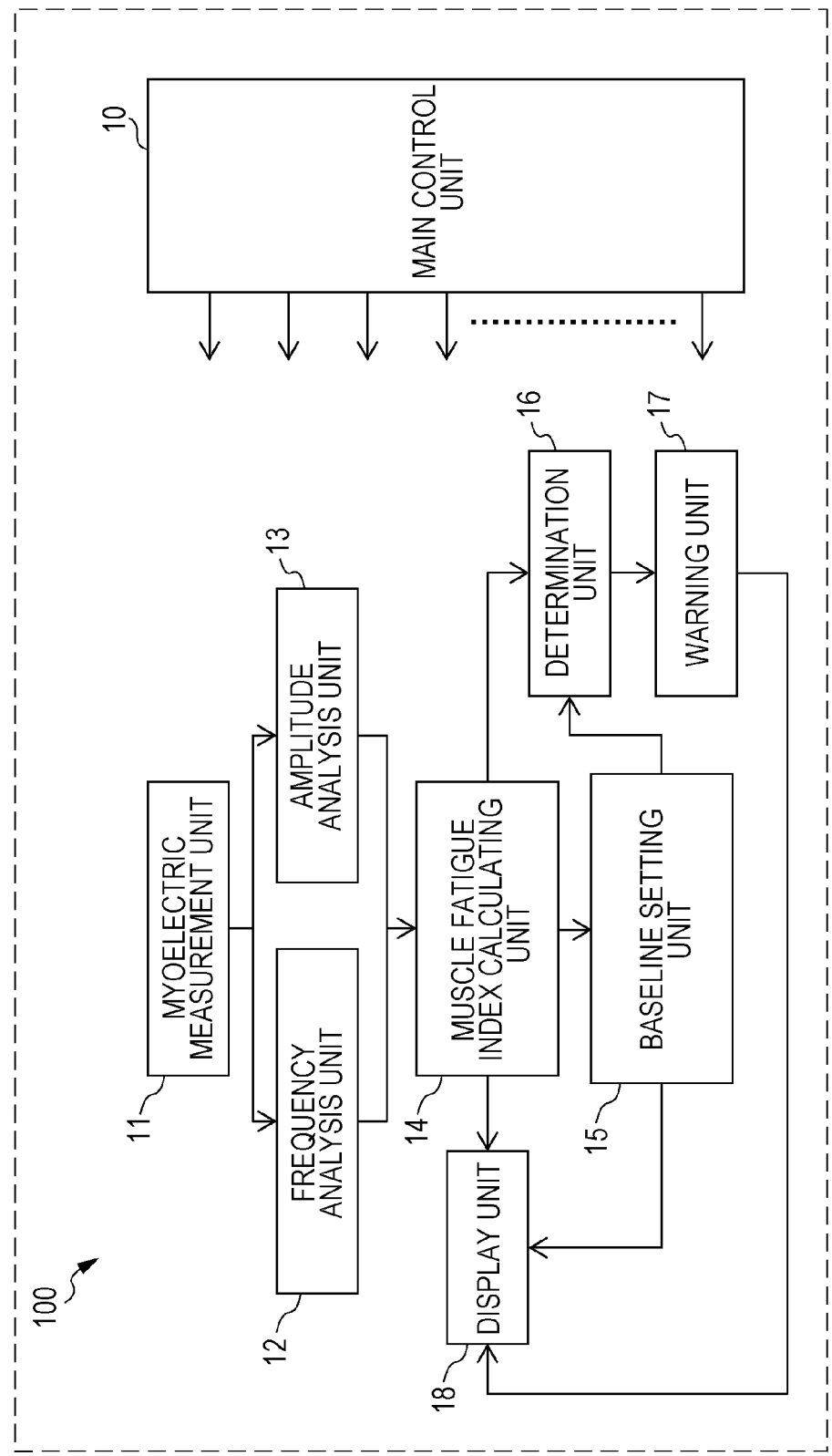
FIG. 38 is a block diagram depicting a configuration of a muscle fatigue output device according to embodiment 1.

Next, a configuration of a muscle fatigue output device 100 for realizing the muscle fatigue output method according to the present embodiment will be described. FIG. 38 depicts a configuration of the muscle fatigue output device 100 according to embodiment 1. The muscle fatigue output device 100 is provided with a main control unit 10, a myoelectric measurement unit 11, a frequency analysis unit 12, an amplitude analysis unit 13, a muscle fatigue index calculating unit 14, a baseline setting unit 15, a determination unit 16, a warning unit 17, and a display unit 18.

(Main Control Unit 10)

The main control unit 10 controls all operations of the muscle fatigue output device 100. Specifically, the main control unit 10 controls the operations of the myoelectric measurement unit 11, the frequency analysis unit 12, the amplitude analysis unit 13, the muscle fatigue index calculating unit 14, the baseline setting unit 15, the determination unit 16, the warning unit 17, and the display unit 18. The main control unit 10 may be combined with any of the frequency analysis unit 12, the amplitude analysis unit 13, the muscle fatigue index calculating unit 14, the baseline setting unit 15, and the determination unit 16. The main control unit 10 may be incorporated in the arithmetic unit 5 depicted in FIG. 3, for example. Here, the main control unit 10, the frequency analysis unit 12, the amplitude analysis unit 13, the muscle fatigue index calculating unit 14, the baseline setting unit 15, and the determination unit 16 are examples of control units.

(Myoelectric Measurement Unit 11)

The myoelectric measurement unit 11 measures the myoelectric potentials of a target muscle. The myoelectric measurement unit 11 is provided with a bioelectric potential sensor that is attached to the skin covering the target muscle. The bioelectric potential sensor is provided with an electrode that is attached to the skin covering the target muscle, and a measurement circuit that measures myoelectric potentials constituting muscular action potentials of the target muscle by way of the electrode. For example, the bioelectric potential sensor measures the myoelectric potentials of the target muscle through a surface electrode of the bioelectric potential sensor that is affixed to the skin covering the target muscle. The electrode of the bioelectric potential sensor may be a needle electrode or a wire electrode that is inserted into the skin. The bioelectric potential sensor of the myoelectric measurement unit 11 may be the electrodes 2 depicted in FIG. 3. The myoelectric measurement unit 11 may have a configuration provided with the electrodes 2, may have a configuration provided with the electrodes 2 and the acceleration sensor 3, or may have a configuration provided with the signal processor 4 and at least the electrodes 2 from among the electrodes 2 and the acceleration sensor 3. Here, the myoelectric measurement unit 11 is an example of a myoelectric sensor.

(Frequency Analysis Unit 12)

The frequency analysis unit 12 analyzes frequency characteristics of myoelectric potentials for each predetermined time. The frequency analysis unit 12 analyzes frequency characteristics of myoelectric potentials from measurement results for myoelectric potentials from within the predetermined times. In this case, the frequency analysis unit 12 sets a plurality of predetermined times to be successive, and analyzes frequency characteristics of myoelectric potentials for each predetermined time. The plurality of predetermined times may or may not overlap with each other. A parameter obtained from the frequency characteristics analysis is the mean frequency (MNF), the median frequency (MDF), or the like. It should be noted that a predetermined number of cycles of myoelectric potentials may be used instead of the predetermined times. The frequency analysis unit 12 may be incorporated in the arithmetic unit 5 depicted in FIG. 3, for example.

(Amplitude Analysis Unit 13)

The amplitude analysis unit 13 analyzes amplitude characteristics of myoelectric potentials for each predetermined time. The amplitude analysis unit 13 analyzes amplitude characteristics of myoelectric potentials from measurement results for myoelectric potentials from within the predetermined times. In this case, the amplitude analysis unit 13 sets a plurality of predetermined times to be successive, and analyzes amplitude characteristics of myoelectric potentials for each predetermined time. The plurality of predetermined times may or may not overlap with each other. A parameter obtained from the amplitude characteristics analysis is the average rectified value (ARV), the root mean square (RMS), or the like. The amplitude analysis unit 13 may be incorporated in the arithmetic unit 5 depicted in FIG. 3, for example.

(Muscle Fatigue Index Calculating Unit 14)

The muscle fatigue index calculating unit 14 calculates, as an index for muscle fatigue, the ratio between a parameter value for a frequency characteristic acquired by the frequency analysis unit 12 and a parameter value for an amplitude characteristic acquired by the amplitude analysis unit 13. The muscle fatigue index calculating unit 14 uses MNF/ARV as a muscle fatigue index, for example. The muscle fatigue index calculating unit 14 may be incorporated in the arithmetic unit 5 depicted in FIG. 3, for example.

(Baseline Setting Unit 15)

The baseline setting unit 15, with regard to the muscle fatigue index, sets a baseline that divides between a muscle fatigue determination region and a muscle fatigue non-determination region. To determine the baseline value, the muscle fatigue index value that is initially output by the muscle fatigue index calculating unit 14, the initial MNF/ARV value, for example, may be used. Additionally, to determine the baseline value, after measurement of myoelectric potentials by the myoelectric measurement unit 11 has started, the slope of MNF/ARV in the initial predetermined time may be used. This predetermined time may be changed according to the weight of the load. The baseline setting unit 15 may be incorporated in the arithmetic unit 5 depicted in FIG. 3, for example.

(Determination Unit 16)

The determination unit 16 determines that the muscle fatigue state is in effect when the ratio between the parameter value for a frequency characteristic acquired by the frequency analysis unit 12 and the parameter value for an amplitude characteristic acquired by the amplitude analysis unit 13, namely the muscle fatigue index value, is within the muscle fatigue determination region. For example, when MNF/ARV is used as the muscle fatigue index, the muscle fatigue state is determined as being in effect when MNF/ARV has fallen below the baseline.

It should be noted that in order to cope with fluctuations in MNF/ARV corresponding to an individual person, the determination unit 16 may determine that the muscle fatigue state is in effect when MNF/ARV has fallen below the baseline and has then either continued to remain below the baseline for a predetermined time or has fallen below the baseline a predetermined number of times. The predetermined time and the predetermined number of times may be determined on the basis of the initial value for MNF/ARV. For example, if the initial value for MNF/ARV is large, the predetermined time is increased and the predetermined number of times is increased. The time during which counting is performed for the predetermined number may be restricted or may not be restricted. Furthermore, the predetermined time and the predetermined number of times may be determined according to the baseline value. For example, if the baseline is large, the predetermined time is increased and the predetermined number of times is increased. The determination unit 16 may be incorporated in the arithmetic unit 5 depicted in FIG. 3, for example.

(Warning Unit 17)

The warning unit 17 warns the measurement subject, namely the user, if the determination unit 16 has determined that the muscle fatigue state is in effect. A warning is displayed on a screen or a warning sound is generated as the warning method. The warning unit 17 may be incorporated in the arithmetic unit 5 depicted in FIG. 3 and use a screen display device, a sound generation device, or the like of the arithmetic unit 5, or may be a device or part of a device provided separately from the arithmetic unit 5, for example.

(Display Unit 18)

Figure 40:
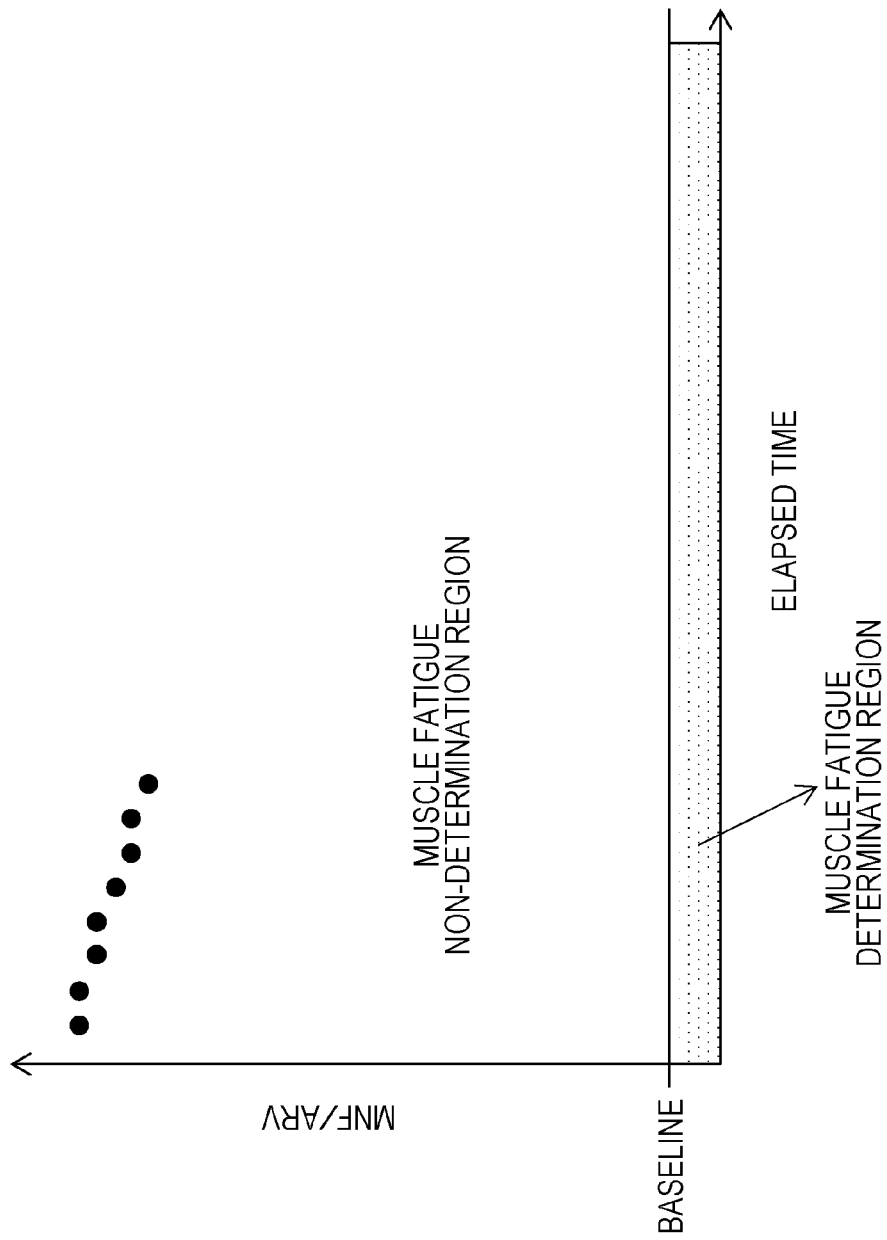
FIG. 40 is a drawing depicting an example of processing results being displayed by the muscle fatigue output device according to embodiment 1.

The display unit 18 displays various information. For example, the display unit 18 plots and displays, together with the baseline, changes over time in the value of the muscle fatigue index, which is the ratio between the parameter value for a frequency characteristic acquired by the frequency analysis unit 12 and the parameter value for an amplitude characteristic acquired by the amplitude analysis unit 13. FIG. 40 depicts an example of the aforementioned display implemented by the display unit 18. It should be noted that the display unit 18 may display a determination result of the determination unit 16 and a warning of the warning unit 17. The hardware constituting the display unit 18 is a liquid crystal display or an organic electro-luminescence (EL) display, for example. The display unit 18 may be incorporated in the arithmetic unit 5 depicted in FIG. 3 and use a screen display device or the like of the arithmetic unit 5, or may be a device or part of a device provided separately from the arithmetic unit 5, for example.

The constituent elements of the main control unit 10, the frequency analysis unit 12, the amplitude analysis unit 13, the muscle fatigue index calculating unit 14, the baseline setting unit 15, and the determination unit 16 such as the aforementioned may be constituted by a microcomputer or other dedicated hardware provided in a device such as the arithmetic unit 5 depicted in FIG. 3, a medical device, a health care device, a sports device, a fitness device, or a training device, for example. Furthermore, for example, the aforementioned constituent elements may be realized by executing a software program suitable for each constituent element. In this case, the aforementioned constituent elements may be provided with a computation processing unit and a storage unit that stores a control program, for example. An example of a computation processing unit is a microprocessing unit (MPU), a central processing unit (CPU), or the like. An example of the storage unit is a memory or the like. It should be noted that all of the aforementioned constituent elements may be constituted by an individual control element that performs centralized control, or may be constituted by a plurality of control elements that cooperate with each other to perform distributed control.

It should be noted that the arithmetic unit 5 may be a small portable device rather than a device of the type that is used in a placed state as disclosed in FIG. 3, for example, a mobile terminal such as a smartphone or a tablet, or a small dedicated device. Alternatively, the arithmetic unit 5 may be incorporated as part of another device. The arithmetic unit 5 may include the signal processor 4.

For example, in the case where the arithmetic unit 5 is capable of accessing a communication network such as the Internet in a manner similar to a personal computer or a mobile terminal such as a smartphone, the constituent elements of the main control unit 10, the frequency analysis unit 12, the amplitude analysis unit 13, the muscle fatigue index calculating unit 14, the baseline setting unit 15, and the determination unit 16 may be realized by executing programs provided as applications in the arithmetic unit 5 via the communication network.

(1-3. Entire Processing Flow)

Figure 39:
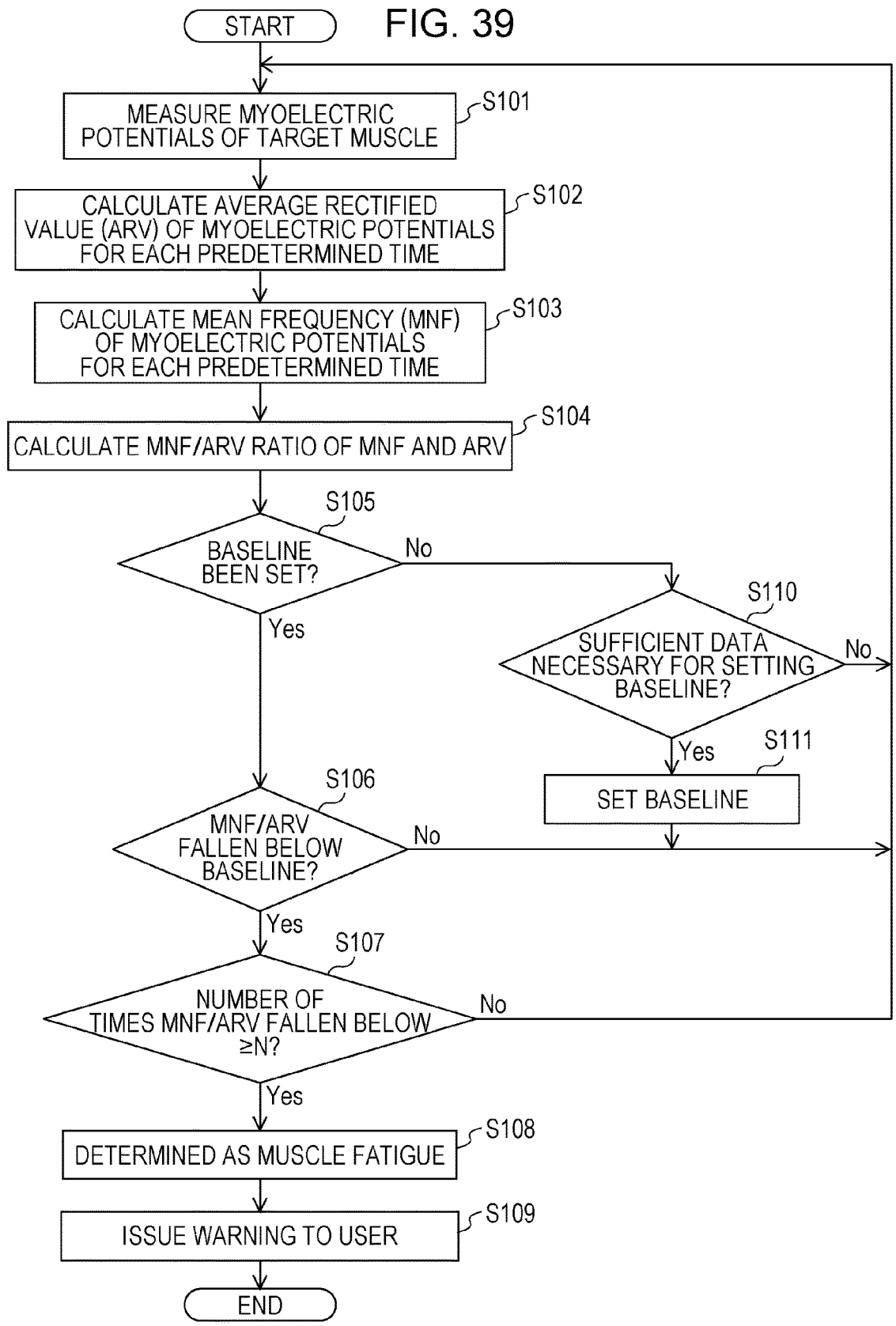
FIG. 39 is a flowchart depicting an example of a processing flow of the muscle fatigue output device according to embodiment 1.

Next, an example of the operation of the muscle fatigue output device 100 according to the present embodiment will be described with reference to FIG. 39. FIG. 39 depicts an example of a processing flow for the output of information regarding muscle fatigue performed by the muscle fatigue output device 100 according to the present embodiment.

<Step S101>

The myoelectric measurement unit 11 is attached to the skin covering the target muscle of the measurement subject, and starts measuring the myoelectric potentials of the target muscle.

<Step S102>

After measurement has started, the amplitude analysis unit 13, for each fourth predetermined time constituting a predetermined time, calculates the average rectified value (ARV) of the myoelectric potentials measured by the myoelectric measurement unit 11 within the fourth predetermined time.

<Step S103>

After measurement has started, the frequency analysis unit 12, for each fourth predetermined time, calculates the mean frequency (MNF) of the myoelectric potentials measured by the myoelectric measurement unit 11 within the fourth predetermined time.

<Step S104>

The muscle fatigue index calculating unit 14 uses the ARV and the MNF calculated by the amplitude analysis unit 13 and the frequency analysis unit 12 to calculate MNF/ARV, the ratio between the MNF and ARV, for each fourth predetermined time.

<Step S105>

Next, the baseline setting unit 15 determines whether or not a baseline has already been set. If already set (yes in step S105), the baseline setting unit 15 proceeds to step S106. If not set (no in step S105), the baseline setting unit 15 proceeds to step S110.

<Step S106>

The determination unit 16 determines whether or not MNF/ARV has fallen below the set baseline. If MNF/ARV has fallen below the set baseline (yes in step S106), the determination unit 16 proceeds to step S107. If MNF/ARV has not fallen below the set baseline (no in step S106), the determination unit 16 proceeds to step S101.

<Step S107>

The determination unit 16 determines whether or not the number of times that MNF/ARV has fallen below the baseline is equal to or greater than a predetermined number of times N. If the number of times that MNF/ARV has fallen below the baseline is equal to or greater than the predetermined number of times N (yes in step S107), the determination unit 16 proceeds to step S108. If the number of times that MNF/ARV has fallen below the baseline is less than the predetermined number of times N (no in step S107), the determination unit 16 proceeds to step S101. N is an integer that is equal to or greater than 1. It should be noted that the determination unit 16 may determine "no" in step S107 even when the number of times that MNF/ARV has fallen below the baseline has reached the predetermined number of times N, if the number of times that MNF/ARV has fallen below the baseline has not reached the predetermined number of times within a predetermined time. Alternatively, the determination unit 16 may determine "no" in step S107 if the $N^{th}$ count is made after a state in which MNF/ARV does not fall below the baseline has continued for a predetermined time or longer from it being counted that MNF/ARV has fallen below the baseline for the $N-1^{th}$ time.

<Step S108>

The determination unit 16 determines that the target muscle of the measurement subject is in the muscle fatigue state.

<Step S109>

The warning unit 17 warns the measurement subject that the muscle fatigue state is in effect, on the basis of the muscle fatigue state determination by the determination unit 16.

<Step S110>

The baseline setting unit 15 determines whether or not the data necessary for setting the baseline is sufficient. If the data is sufficient (yes in step S110), the baseline setting unit 15 proceeds to step S111. If the data is not sufficient (no in step S110), the baseline setting unit 15 proceeds to step S101. For example, when the aforementioned expression (1) is used to set the baseline, the data necessary to set the baseline may be one or more initial values for MNF/ARV. When the aforementioned expression (2) is used to set the baseline, the data necessary to set the baseline may be two or more values for MNF/ARV and the time corresponding thereto necessary for the calculation of the slope for the linear approximation equation for MNF/ARV.

<Step S111>

The baseline setting unit 15 sets the baseline using the necessary data. The baseline setting unit 15 then proceeds to step S101.

(1-4. Description of Effect)

As mentioned above, the muscle fatigue output device 100 according to embodiment 1 is provided with the myoelectric measurement unit 11 that acquires myoelectricity of the user, and the main control unit 10 that determines fatigue of a muscle of the user on the basis of the myoelectricity. The main control unit 10 (a) uses the myoelectricity to acquire a value for a frequency characteristic of the myoelectricity, (b) uses the myoelectricity to acquire a value for an amplitude characteristic of the myoelectricity, (c) acquires a ratio between the value for the frequency characteristic and the value for the amplitude characteristic as an index for the fatigue of the muscle of the user, and (d) outputs information that is based on the index for the fatigue of the muscle of the user. The user is the person using the muscle fatigue output device 100.

In the aforementioned configuration, the ratio between the value for the frequency characteristic and the value for the amplitude characteristic that serves as the index for the fatigue of the muscle of the user reflects the fatigue state of the muscle from which the myoelectric measurement unit 11 acquires myoelectricity, and does not reflect the fatigue state of muscles from which the myoelectric measurement unit 11 does not acquire myoelectricity. For example, when the myoelectric measurement unit 11 acquires myoelectricity of the biceps, the ratio between the value for the frequency characteristic and the value for the amplitude characteristic reflects the fatigue state of the biceps and does not reflect the fatigue state of the triceps. In addition, the ratio between the value for the frequency characteristic and the value for the amplitude characteristic indicates a decreasing or increasing trend in accordance with the fatigue of the muscle. Although the ratio between the value for the frequency characteristic and the value for the amplitude characteristic may be acquired from the myoelectricity included in one or more cycles when the user repeatedly performs an exercise, the aforementioned characteristic of the ratio between the value for the frequency characteristic and the value for the amplitude characteristic is a characteristic in which the effect of the number of cycles used for acquisition is suppressed to be low. Thus, it is possible to reduce the effect from the exercise situation of the user and to output muscle fatigue information having a high degree of accuracy.

In the muscle fatigue output device 100 according to embodiment 1, the main control unit 10, in step (a), uses the myoelectricity to calculate a mean frequency, or uses the myoelectricity to calculate a median frequency, as the value for the frequency characteristic of the myoelectricity. The aforementioned characteristic of the ratio between the value for the frequency characteristic and the value for the amplitude characteristic can be obtained regardless of whether the mean frequency or the median frequency is used as the value for the frequency characteristic of the myoelectricity.

In the muscle fatigue output device 100 according to embodiment 1, the main control unit 10, in step (b), calculates an average rectified value using the myoelectricity, or calculates a root mean square using the myoelectricity, as the value for the amplitude characteristic of the myoelectricity. The aforementioned characteristic of the ratio between the value for the frequency characteristic and the value for the amplitude characteristic can be obtained regardless of whether the average rectified value or the root mean square is used as the value for the amplitude characteristic of the myoelectricity.

In the muscle fatigue output device 100 according to embodiment 1, the main control unit 10 (e) determines whether or not the muscle of the user is fatigued, according to whether or not the ratio between the value for the frequency characteristic and the value for the amplitude characteristic is equal to or greater than a baseline value serving as a first threshold value, and outputs information indicating whether or not the muscle of the user is fatigued, as the information mentioned in step (d). The determination as to whether or not the muscle of the user is fatigued is thereby facilitated. In addition, the user is able to clearly understand the fatigue state of his or her own muscle.

The muscle fatigue output device 100 according to embodiment 1 is provided with the myoelectric measurement unit 11 that acquires myoelectricity of the user, and the main control unit 10 that determines fatigue of a muscle of the user on the basis of the myoelectricity. The main control unit 10 (a) uses the myoelectricity to acquire a value for a frequency characteristic of the myoelectricity, (b) uses the myoelectricity to acquire a value for an amplitude characteristic of the myoelectricity, (c) acquires a ratio between the value for the frequency characteristic and the value for the amplitude characteristic as an index for the fatigue of the muscle of the user, (d) outputs information that is based on the index for the fatigue of the muscle of the user, the information indicating whether or not the muscle of the user is fatigued, and (e) determines whether or not the muscle of the user is fatigued, according to whether or not the ratio between the value for the frequency characteristic and the value for the amplitude characteristic is equal to or greater than a baseline value serving as a first threshold value. The user is the person using the muscle fatigue output device 100. The myoelectric measurement unit 11 may acquire first myoelectricity of the user at a first time, and second myoelectricity of the user at a second time subsequent to the first time. In addition, the main control unit 10, prior to step (e), (f) may change the baseline value serving as the first threshold value, on the basis of the first myoelectricity and the second myoelectricity. In this case, the main control unit 10, in step (a), may use the first myoelectricity to acquire a value for a frequency characteristic of the first myoelectricity, and use the second myoelectricity to acquire a value for a frequency characteristic of the second myoelectricity, in step (b), may use the first myoelectricity to acquire a value for an amplitude characteristic of the first myoelectricity, and use the second myoelectricity to acquire a value for an amplitude characteristic of the second myoelectricity, and, in step (c), may acquire a first ratio between the value for the frequency characteristic of the first myoelectricity and the value for the amplitude characteristic of the first myoelectricity, and acquire a second ratio between the value for the frequency characteristic of the second myoelectricity and the value for the amplitude characteristic of the second myoelectricity, as indexes for the fatigue of the muscle of the user. In addition, the main control unit 10, in step (f), may change the baseline value on the basis of a change in the first ratio and the second ratio, and, in step (e), may determine whether or not the muscle of the user is fatigued, according to whether or not at least one of the first ratio and the second ratio is equal to or greater than the changed baseline value.

In the aforementioned configuration, a change in the two ratios between values for the frequency characteristic and values for the amplitude characteristic obtained at the two times may indicate the effect that a load acting on the muscle of the user has on the muscle of the user, namely whether the load is large or small. The time taken for the muscle to be fatigued changes according to the size of the load. Thus, the baseline value that is changed on the basis of a change in the ratios indicates the fatigue state of the muscle with a high degree of accuracy.

In the muscle fatigue output device 100 according to embodiment 1, the main control unit 10, as step (f) prior to step (e), changes the baseline value serving as the first threshold value, on the basis of the ratio between the value for the frequency characteristic and the value for the amplitude characteristic first acquired in step (c). In the aforementioned configuration, the ratio between the value for the frequency characteristic and the value for the amplitude characteristic first acquired may indicate the effect that a load acting on the muscle of the user has on the muscle of the user, namely whether the load is large or small. Thus, the baseline value that is changed on the basis of a change in the ratio indicates the fatigue state of the muscle with a high degree of accuracy.

It should be noted that in the aforementioned embodiment, the constituent elements may be configured by using dedicated hardware, or may be realized by executing a software program suitable for the constituent elements. The constituent elements may be realized by a program execution device such as a CPU or a processor reading out and executing a software program recorded in a recording medium such as a hard disk or a semiconductor memory. Here, software that realizes the muscle fatigue output device or the like according to the aforementioned embodiment is a program such as the following.

That is, the program is a program that causes a computer to execute, with which (h1) myoelectricity of a user is acquired by the myoelectric measurement unit 11, (h2) a value for a frequency characteristic of the myoelectricity is acquired using the myoelectricity, (h3) a value for an amplitude characteristic of the myoelectricity is acquired using the myoelectricity, (h4) a ratio between the value for the frequency characteristic and the value for the amplitude characteristic is acquired as an index for the fatigue of the muscle of the user, and (h5) information regarding the fatigue of the muscle of the user is output on the basis of the index for the fatigue of the muscle of the user.

Furthermore, in the aforementioned embodiment, the constituent elements may be circuits. The plurality of constituent elements may constitute one circuit in their entirety or may constitute separate circuits. Furthermore, the circuits may be general-purpose circuits or may be dedicated circuits. Here, the muscle fatigue output method or the like according to the aforementioned embodiment is realized by a processor such as the following constituting a circuit.

That is, the muscle fatigue output method is a muscle fatigue output method that is realized by a processor, with which myoelectricity of a user is acquired by the myoelectric measurement unit 11, a value for a frequency characteristic of the myoelectricity is acquired using the myoelectricity, a value for an amplitude characteristic of the myoelectricity is acquired using the myoelectricity, a ratio between the value for the frequency characteristic and the value for the amplitude characteristic is acquired as an index for fatigue of a muscle of the user, and information regarding the fatigue of the muscle of the user is output on the basis of the index for the fatigue of the muscle of the user.

Embodiment 2

In a muscle fatigue output device according to embodiment 2, in addition to evaluating the present muscle fatigue state in embodiment 1, a remaining capacity constituting the exercise capacity remaining until the user fatigues is estimated on the basis of a baseline value and an MNF/ARV value constituting the present muscle fatigue index, and is displayed to the user. Hereinafter, embodiment 2 will be described focusing on the differences with embodiment 1.

(2-1. Configuration of Muscle Fatigue Output Device)

Figure 41:
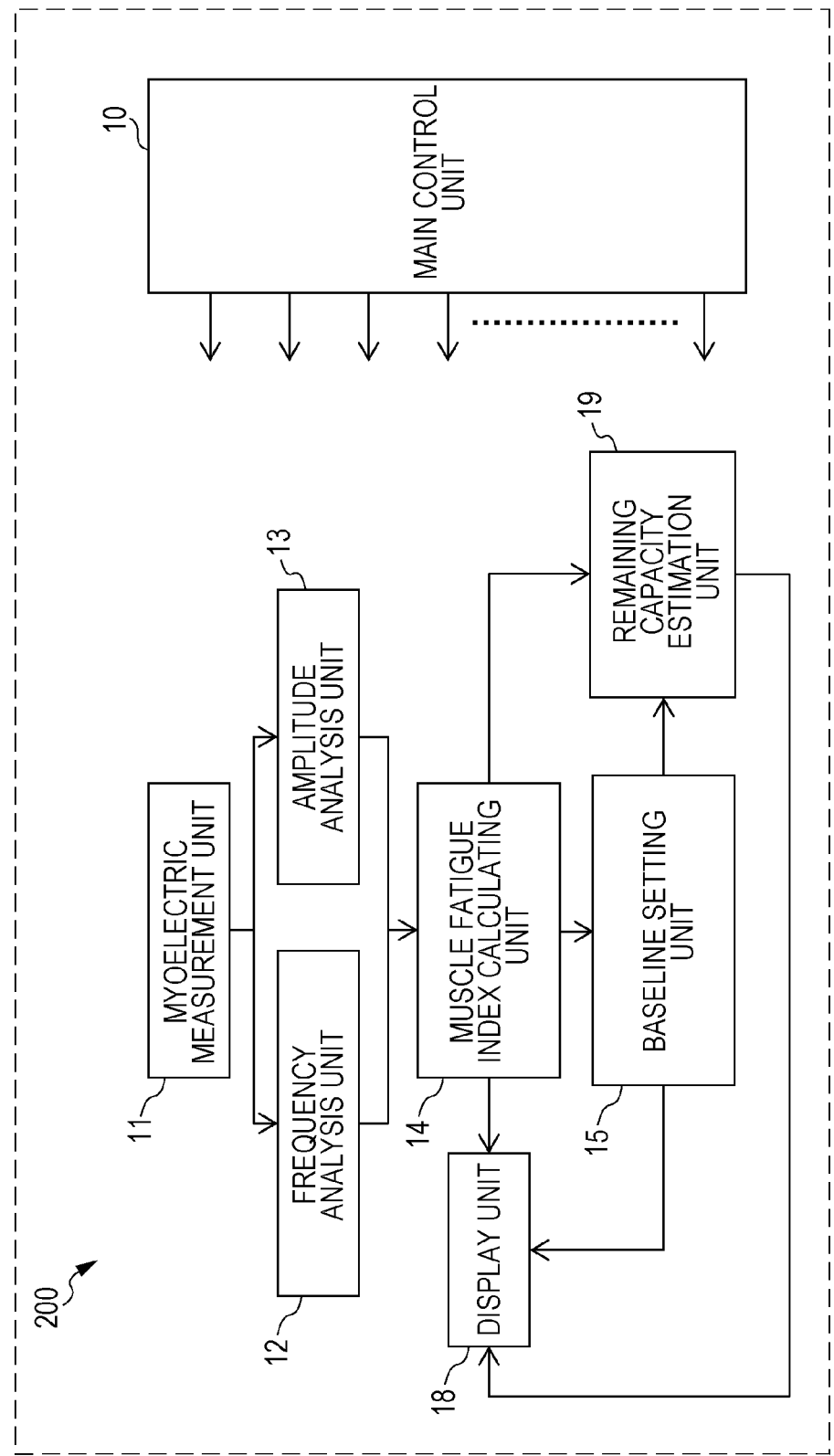
FIG. 41 is a block diagram depicting a configuration of a muscle fatigue output device according to embodiment 2.

FIG. 41 depicts a configuration of a muscle fatigue output device 200 according to embodiment 2. The muscle fatigue output device 200 is provided with a main control unit 10, a myoelectric measurement unit 11, a frequency analysis unit 12, an amplitude analysis unit 13, a muscle fatigue index calculating unit 14, a baseline setting unit 15, and a display unit 18 that are the same as in embodiment 1, and a remaining capacity estimation unit 19. The configurations and operations of the myoelectric measurement unit 11, the frequency analysis unit 12, the amplitude analysis unit 13, the muscle fatigue index calculating unit 14, and the baseline setting unit 15 are the same as in embodiment 1, and therefore descriptions thereof have been omitted.

(Main Control Unit 10)

The main control unit 10 controls all operations of the muscle fatigue output device 200. Specifically, the main control unit 10 controls the myoelectric measurement unit 11, the frequency analysis unit 12, the amplitude analysis unit 13, the muscle fatigue index calculating unit 14, the baseline setting unit 15, the display unit 18, and the remaining capacity estimation unit 19. The main control unit 10 may be combined with any of the myoelectric measurement unit 11, the frequency analysis unit 12, the amplitude analysis unit 13, the muscle fatigue index calculating unit 14, the baseline setting unit 15, and the remaining capacity estimation unit 19.

(Remaining Capacity Estimation Unit 19)

The remaining capacity estimation unit 19 estimates a fatigue time, which is the time until falling below the baseline, on the basis of the present muscle fatigue index MNF/ARV value and the baseline value. It should be noted that the present MNF/ARV value is the most recently calculated MNF/ARV value. As a method for estimating fatigue time, the remaining capacity estimation unit 19 linearly approximates the relationship between a plurality of MNF/ARV values, which are either values up to the present point in time or are the most recent values, and the time corresponding to the plurality of MNF/ARV values, and calculates the time at which the line obtained by the linear approximation intersects the baseline. The remaining capacity estimation unit 19 then sets a value obtained by subtracting the present time from the time at which the baseline is intersected, as the fatigue time. In addition, the remaining capacity estimation unit 19 estimates, on the basis of the fatigue time, a remaining number of times that constitutes the number of times that the user can still perform a cycle of the exercise. One cycle of the exercise is one cycle of a repeated exercise such as the bending and stretching exercise of the elbow given in the aforementioned experiments, for example. The remaining number of times can be a value obtained by dividing the fatigue time by the time necessary for one cycle of the exercise.

(Display Unit 18)

The display unit 18, in addition to that displayed in embodiment 1, displays the fatigue time and/or the remaining number of times calculated by the remaining capacity estimation unit 19.

(2-2. Muscle Fatigue Estimation Processing Flow)

Figure 42:
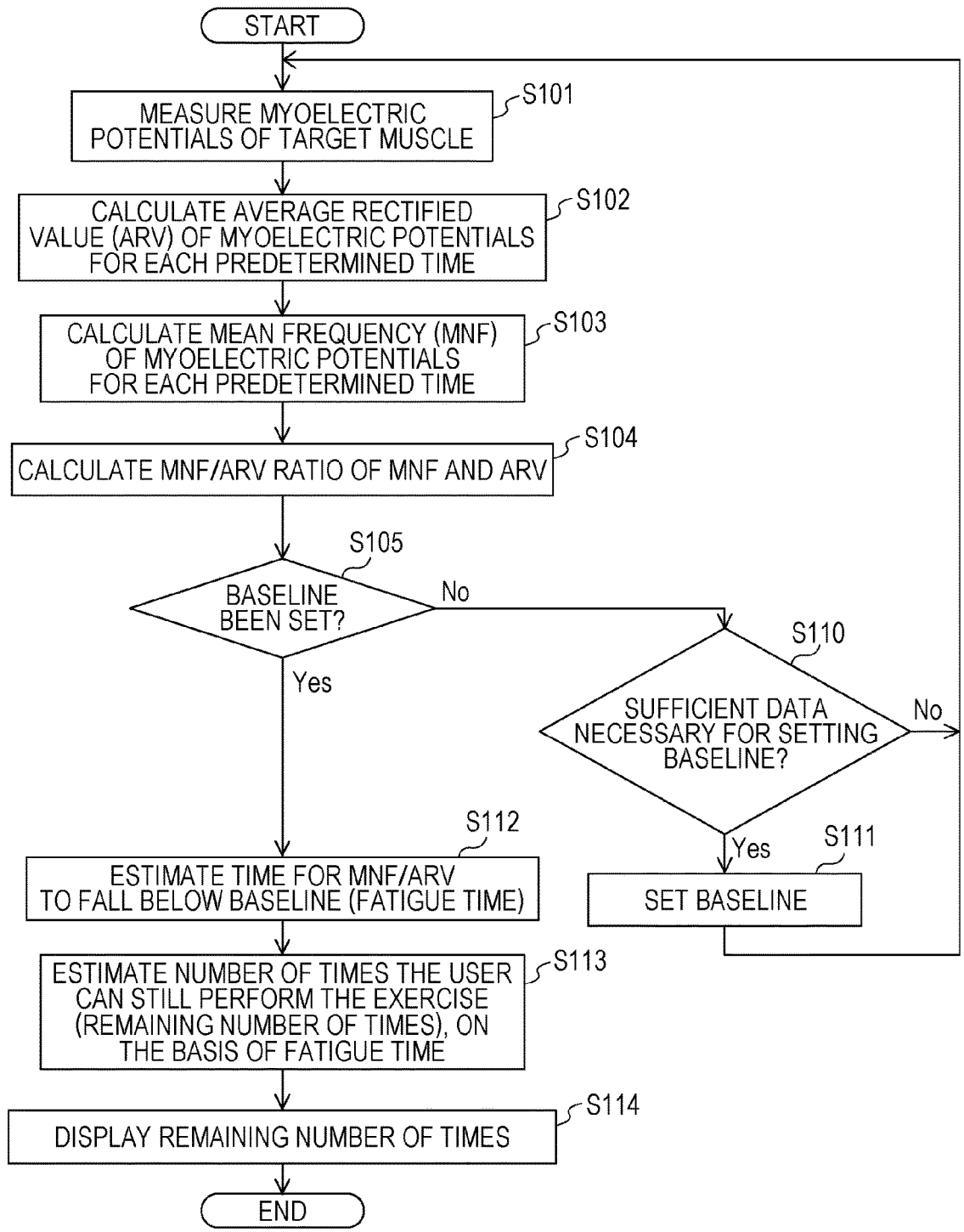
FIG. 42 is a flowchart depicting an example of a processing flow of the muscle fatigue output device according to embodiment 2.

Next, an example of the operation of the muscle fatigue output device 200 according to the present embodiment will be described with reference to FIG. 42. FIG. 42 depicts an example of a processing flow for a muscle fatigue estimation performed by the muscle fatigue output device 200 according to the present embodiment. Steps S101 to S105 and steps S110 and S111 are the same as in embodiment 1, and therefore descriptions thereof have been omitted.

<Step S112>

In step S105, if the baseline has already set (yes in step S105), the remaining capacity estimation unit 19 estimates the fatigue time, which is the time until MNF/ARV falls below the baseline.

<Step S113>

Next, the remaining capacity estimation unit 19 estimates, on the basis of the estimated fatigue time, the remaining number of times constituting the number of times that the user can still perform a cycle of the exercise, the user being the person who is exercising and using the muscle fatigue output device 200.

<Step S114>

The display unit 18 displays the remaining number of times that the user can still perform the exercise, on the basis of the remaining number of times estimated by the remaining capacity estimation unit 19.

(2-3. Description of Effect)

As mentioned above, in the muscle fatigue output device 200 according to embodiment 2, the myoelectric measurement unit 11 acquires third myoelectricity of the user at a third time, and fourth myoelectricity of the user at a fourth time subsequent to the third time. In addition, the main control unit 10 (e) determines whether or not the muscle of the user is fatigued, according to whether or not the ratio between the value for the frequency characteristic and the value for the amplitude characteristic is equal to or greater than the baseline value serving as a first threshold value. Then, the main control unit 10, in step (a), uses the third myoelectricity to acquire a value for a frequency characteristic of the third myoelectricity, and uses the fourth myoelectricity to acquire a value for a frequency characteristic of the fourth myoelectricity, and, in step (b), uses the third myoelectricity to acquire a value for an amplitude characteristic of the third myoelectricity, and uses the fourth myoelectricity to acquire a value for an amplitude characteristic of the fourth myoelectricity. In addition, the main control unit 10, in step (c), acquires a third ratio between the value for the frequency characteristic of the third myoelectricity and the value for the amplitude characteristic of the third myoelectricity, acquires a fourth ratio between the value for the frequency characteristic of the fourth myoelectricity and the value for the amplitude characteristic of the fourth myoelectricity, as indexes for the fatigue of the muscle of the user, and, in step (g), estimates a time until the ratio between the value for the frequency characteristic and the value for the amplitude characteristic reaches the baseline value, on the basis of changes over time in the third ratio and the fourth ratio. The main control unit 10, in step (d), outputs the result of the estimation performed in step (g), as information regarding the fatigue of the muscle of the user. In addition, the main control unit 10, in step (g), may estimate a movement capacity remaining for the user, on the basis of the estimated time, and, in step (d), may output the movement capacity estimated in step (g).

In the aforementioned configuration, future transitions in the ratio are estimated from changes over time in the two ratios between the values for the frequency characteristic and the values for the amplitude characteristic obtained at the two times. Then, using this estimation, the time until the ratio between the value for a frequency characteristic and the value for the amplitude characteristic reaches the baseline value is estimated. Thus, the user who is exercising is able to obtain information regarding his or her own remaining capacity with respect to muscle fatigue.

Other Modified Examples

A muscle fatigue output device and the like according to one or more aspects have been described heretofore on the basis of embodiments; however, the present disclosure is not limited to these embodiments. Modes in which various modifications conceived by a person skilled in the art have been implemented in the present embodiments, and modes constructed by combining the constituent elements in different embodiments may also be included within the scope of the one or more aspects provided they do not depart from the purpose of the present disclosure.

The muscle fatigue output devices 100 and 200 according to embodiments 1 and 2 output information regarding the muscle fatigue of an arm of a person; however, information regarding the muscle fatigue of any part of a person may be output.

The muscle fatigue output device, muscle fatigue output method, and recording medium according to the present disclosure can be applied in fields such as medicine, health care, sports, fitness, and training.

What is claimed is:

1. A muscle fatigue output device, comprising:
a myoelectric sensor that acquires myoelectricity of a user; and
a controller,
the controller:
(a) using the myoelectricity to acquire a value for a frequency characteristic of the myoelectricity;
(b) using the myoelectricity to acquire a value for an amplitude characteristic of the myoelectricity;
(c) acquiring a ratio between the value for the frequency characteristic and the value for the amplitude characteristic as an index for fatigue of a muscle of the user;
(d) outputting information that is based on the index for the fatigue of the muscle of the user; and
(e) determining whether or not the muscle of the user is fatigued, according to whether or not the ratio between the value for the frequency characteristic and the value for the amplitude characteristic is equal to or greater than a first threshold value,
wherein the information indicates whether or not the muscle of the user is fatigued.

2. The muscle fatigue output device according to claim 1, wherein the controller, in (a), uses the myoelectricity to calculate a mean frequency as the value for the frequency characteristic of the myoelectricity.

3. The muscle fatigue output device according to claim 1, wherein the controller, in (a), uses the myoelectricity to calculate a median frequency as the value for the frequency characteristic of the myoelectricity.

4. The muscle fatigue output device according to claim 1, wherein the controller, in (b), uses the myoelectricity to calculate an average rectified value as the value for the amplitude characteristic of the myoelectricity.

5. The muscle fatigue output device according to claim 1, wherein the controller, in (b), uses the myoelectricity to calculate a root mean square as the value for the amplitude characteristic of the myoelectricity.

6. The muscle fatigue output device according to claim 1, wherein the controller additionally includes, prior to (e), (f) changing the first threshold value on the basis of the ratio between the value for the frequency characteristic and the value for the amplitude characteristic first acquired in (c).

7. The muscle fatigue output device according to claim 1, wherein the myoelectric sensor acquires a third myoelectricity of the user at a third time and a fourth myoelectricity of the user at a fourth time subsequent to the third time,
the controller additionally includes (e) determining whether or not the muscle of the user is fatigued, according to whether or not the ratio between the value for the frequency characteristic and the value for the amplitude characteristic is equal to or greater than a first threshold value, and
the controller,
in (a), uses the third myoelectricity to acquire a value for a frequency characteristic of the third myoelectricity, and uses the fourth myoelectricity to acquire a value for a frequency characteristic of the fourth myoelectricity,
in (b), uses the third myoelectricity to acquire a value for an amplitude characteristic of the third myoelectricity, and uses the fourth myoelectricity to acquire a value for an amplitude characteristic of the fourth myoelectricity,
in (c), acquires a third ratio between the value for the frequency characteristic of the third myoelectricity and the value for the amplitude characteristic of the third myoelectricity, and a fourth ratio between the value for the frequency characteristic of the fourth myoelectricity and the value for the amplitude characteristic of the fourth myoelectricity, as indexes for the fatigue of the muscle of the user,
in (g), estimates a time until the ratio between the value for the frequency characteristic and the value for the amplitude characteristic reaches the first threshold value, on the basis of changes over time in the third ratio and the fourth ratio, and,
in (d), outputs an estimation result obtained in (g), as information regarding the fatigue of the muscle of the user.

8. The muscle fatigue output device according to claim 7, wherein the controller,
in (g), estimates a movement capacity remaining for the user, on the basis of the estimated time, and,
in (d), outputs the movement capacity estimated in (g).

9. A muscle fatigue output device, comprising:
a myoelectric sensor that acquires myoelectricity of a user; and
a controller,
the controller:
(a) using the myoelectricity to acquire a value for a frequency characteristic of the myoelectricity;
(b) using the myoelectricity to acquire a value for an amplitude characteristic of the myoelectricity;
(c) acquiring a ratio between the value for the frequency characteristic and the value for the amplitude characteristic as an index for fatigue of a muscle of the user;
(d) outputting information that is based on the index for the fatigue of the muscle of the user, the information indicating whether or not the muscle of the user is fatigued; and
(e) determining whether or not the muscle of the user is fatigued, according to whether or not the ratio between the value for the frequency characteristic and the value for the amplitude characteristic is equal to or greater than a first threshold value,
the myoelectric sensor acquiring a first myoelectricity of the user at a first time and a second myoelectricity of the user at a second time subsequent to the first time,
the controller additionally including, prior to (e), (f) changing the first threshold value on the basis of the first myoelectricity and the second myoelectricity, and
the controller,
in (a), using the first myoelectricity to acquire a value for a frequency characteristic of the first myoelectricity, and using the second myoelectricity to acquire a value for a frequency characteristic of the second myoelectricity,
in (b), using the first myoelectricity to acquire a value for an amplitude characteristic of the first myoelectricity, and using the second myoelectricity to acquire a value for an amplitude characteristic of the second myoelectricity,
in (c), acquiring a first ratio between the value for the frequency characteristic of the first myoelectricity and the value for the amplitude characteristic of the first myoelectricity, and acquiring a second ratio between the value for the frequency characteristic of the second myoelectricity and the value for the amplitude characteristic of the second myoelectricity, as indexes for the fatigue of the muscle of the user, in (f), changing the first threshold value on the basis of a change in the first ratio and the second ratio, and, in (e), determining whether or not the muscle of the user is fatigued, according to whether or not at least one of the first ratio and the second ratio is equal to or greater than the changed first threshold value.

10. A recording medium, comprising a control program for causing a device provided with a processor to execute processing, the recording medium being nonvolatile and computer-readable, and the processing including:
(h1) acquiring myoelectricity of a user by using a myoelectric sensor;
(h2) using the myoelectricity to acquire a value for a frequency characteristic of the myoelectricity;
(h3) using the myoelectricity to acquire a value for an amplitude characteristic of the myoelectricity;
(h4) acquiring a ratio between the value for the frequency characteristic and the value for the amplitude characteristic as an index for fatigue of a muscle of a user;
(h5) outputting information that is based on the index for the fatigue of the muscle of the user; and
(h6) determining whether or not the muscle of the user is fatigued, according to whether or not the ratio between the value for the frequency characteristic and the value for the amplitude characteristic is equal to or greater than a first threshold value, wherein the information indicates whether or not the muscle of the user is fatigued.

11. A muscle fatigue output method that is realized by a processor, the muscle fatigue output method including:
acquiring myoelectricity of a user by using a myoelectric sensor;
using the myoelectricity to acquire a value for a frequency characteristic of the myoelectricity;
using the myoelectricity to acquire a value for an amplitude characteristic of the myoelectricity;
acquiring a ratio between the value for the frequency characteristic and the value for the amplitude characteristic as an index for fatigue of a muscle of the user;
outputting information that is based on the index for the fatigue of the muscle of the user; and
determining whether or not the muscle of the user is fatigued, according to whether or not the ratio between the value for the frequency characteristic and the value for the amplitude characteristic is equal to or greater than a first threshold value, wherein the information indicates whether or not the muscle of the user is fatigued.

* * * * *